(12) United States Patent
Schuhmacher et al.

(10) Patent No.: US 6,582,781 B1
(45) Date of Patent: Jun. 24, 2003

(54) MULTILAYER CHOLESTERIC PIGMENTS

(75) Inventors: Peter Schuhmacher, Mannheim (DE);
Norbert Schneider, Altrip (DE);
Volker Richter, Heidelberg (DE);
Harald Keller, Ludwigshafen (DE);
Günter Bettinger, Schifferstadt (DE);
Peter Blaschka, Ludwigshafen (DE);
Peter Heilmann, Bad Dürkhein (DE);
Frank Meyer, Mannhein (DE);
Wolfgang Best, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/486,694

(22) PCT Filed: Sep. 1, 1998

(86) PCT No.: PCT/EP98/05545

§ 371 (c)(1),
(2), (4) Date: Mar. 2, 2000

(87) PCT Pub. No.: WO99/11719

PCT Pub. Date: Mar. 11, 1999

(30) Foreign Application Priority Data

Sep. 2, 1997 (DE) .......................... 197 38 368
Dec. 23, 1997 (DE) .......................... 197 57 699

(51) Int. Cl.$^7$ .............................................. C09K 19/00
(52) U.S. Cl. ....................... 428/1.1; 428/1.2; 428/403; 428/407
(58) Field of Search ................. 428/403, 407, 428/1.1, 1.2

(56) References Cited

U.S. PATENT DOCUMENTS

| | | | |
|---|---|---|---|
| 4,854,262 A | 8/1989 | Chino et al. | |
| 5,211,877 A | 5/1993 | Andrejewski et al. | |
| 5,362,315 A | 11/1994 | Muller-Rees et al. | |
| 5,364,557 A | 11/1994 | Faris | |
| 5,599,412 A | 2/1997 | Faris | |
| 5,780,629 A | 7/1998 | Etzbach et al. | |
| 5,788,880 A | 8/1998 | Schierlinger et al. | |
| 5,827,449 A | 10/1998 | Hanelt et al. | |
| 5,847,068 A | 12/1998 | Maxein et al. | |
| 5,851,277 A | 12/1998 | Muller-Rees et al. | |
| 5,851,604 A * | 12/1998 | Muller-Rees et al. ......... | 428/1 |
| 5,858,097 A | 1/1999 | Richter et al. | |
| 5,876,837 A * | 3/1999 | Sailer et al. ................ | 428/195 |
| 5,886,242 A | 3/1999 | Etzbach et al. | |
| 5,942,030 A | 8/1999 | Schuhmacher et al. | |
| 5,958,125 A * | 9/1999 | Schmid et al. ............... | 106/417 |
| 5,976,239 A | 11/1999 | Dannenhauer et al. | |
| 6,207,770 B1 * | 3/2001 | Coates et al. ................. | 526/63 |
| 6,291,065 B1 * | 9/2001 | Poetsch et al. ............. | 428/363 |

FOREIGN PATENT DOCUMENTS

| | | |
|---|---|---|
| DE | 195 32 408 | 9/1995 |
| DE | 196 39 165 | 6/1997 |
| DE | 196 39 179 | 6/1997 |
| DE | 196 39 229 | 6/1997 |
| DE | 196 02 795 | 7/1997 |
| DE | 196 31 658 | 2/1998 |
| DE | 197 04 506 | 8/1998 |
| DE | 197 13 638 | 10/1998 |
| DE | 197 17 371 | 10/1998 |
| EP | 0 383 376 | 8/1990 |
| EP | 0 431 630 | 6/1991 |
| EP | 0 452 959 | 10/1991 |
| EP | 0 720 753 B1 * | 4/1998 |
| WO | WO 94/22976 | 10/1994 |
| WO | WO 96/02597 | 2/1996 |
| WO | WO 97/00600 | 1/1997 |
| WO | WO 97/30136 | 8/1997 |

OTHER PUBLICATIONS

G.W. Gray, et al., Physico–Chemical Properties and Methods of Investigation, vol. 1, 6 pages, "Liquid Crystals & Plastic Chrystals," 1974 (Table of Contents Only).
H. Baessler, Festkoeperprobleme, Advances in Solid State Physics, vol. 11, pps. 99–132, "Liquid Crystals," 1971.
H. Baessler, et al., The Journal of Chemical Physics, vol. 52, No. 2, pps. 631–637, "Helical Twisting Power of Steriodal Solutes in Cholesteric Mesopahases," Jan. 15, 1970.

* cited by examiner

Primary Examiner—H. Thi Le
(74) Attorney, Agent, or Firm—Oblon, Spivak, McClelland, Maier & Neustadt, P.C.

(57) ABSTRACT

A platelet-shaped cholesteric multilayer pigment which comprises the layer sequence $A^1/B/A^2$
where
$A^1$ and $A^2$ are identical or different and each comprise at least one cholesteric layer, and
B is at least one interlayer which separates the layers $A^1$ and $A^2$ from one another and which absorbs all or some of the light transmitted by the layers $A^1$ and $A^2$,
processes for its preparation, and its use are all described.

14 Claims, 1 Drawing Sheet

MULTILAYER CHOLESTERIC PIGMENTS

Figure 1:
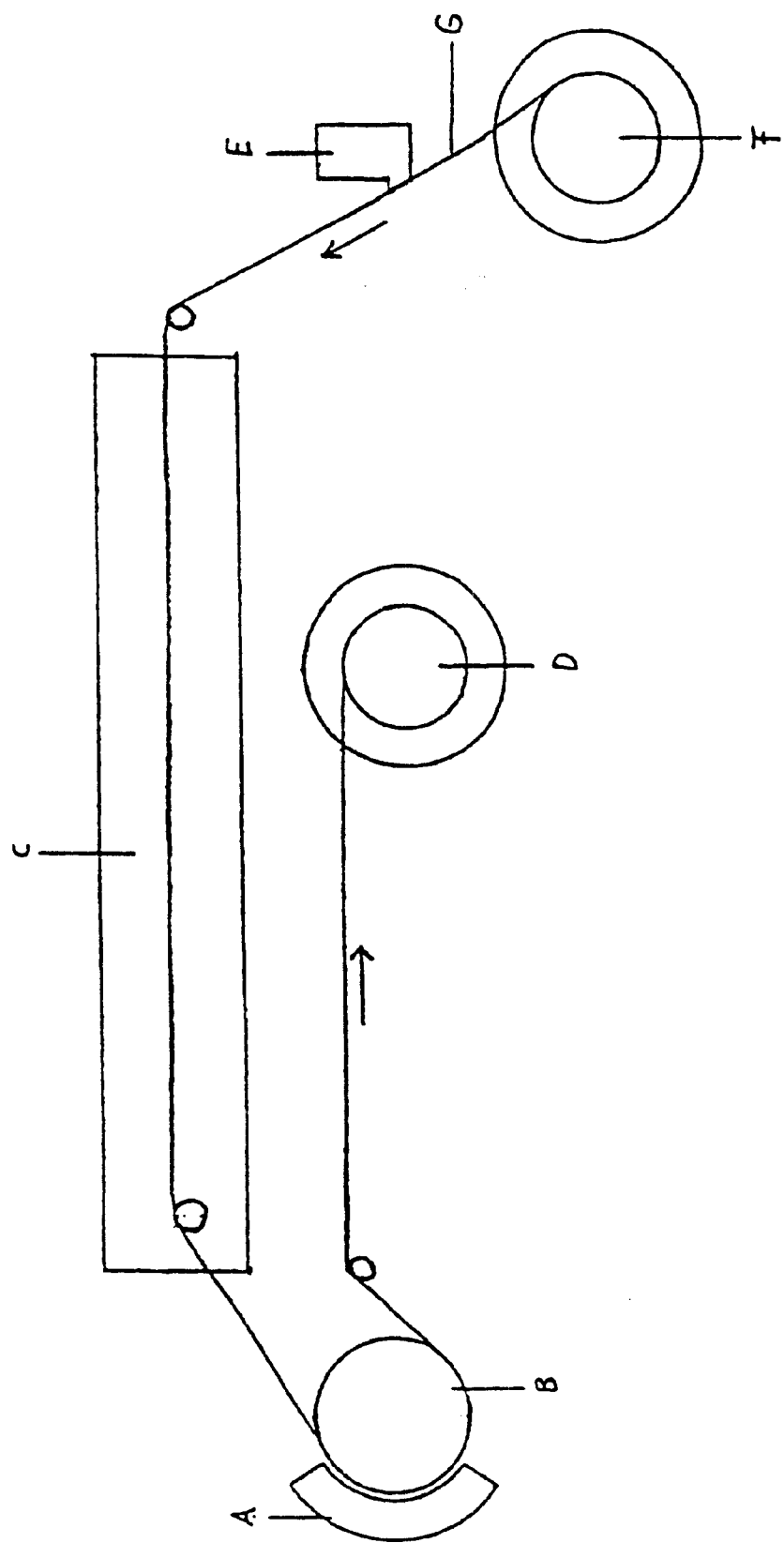

The invention relates to multilayer cholesteric pigments, to processes for their preparation and to their use.

When substances exhibiting shape anisotropy are heated it is possible for liquid-crystalline phases known as mesophases to occur. The individual phases differ in the spatial arrangement of the centers of mass of the molecules, on the one hand, and by the arrangement of the molecules with respect to the long axes, on the other hand (G. W. Gray, P. A. Winsor, Liquid Crystals and Plastic Crystals, Ellis Horwood Limited, Chichester 1974). The nematic liquid-crystalline phase is distinguished by parallel orientation of the long axes of the molecules (one-dimensional order state). Provided that the molecules forming the nematic phase are chiral, the result is a chiral nematic (cholesteric) phase in which the long axes of the molecules form a helical superstructure perpendicular thereto (H. Baessler, Festkörperprobleme XI, 1971). The chiral moiety may be present in the liquid-crystalline molecule itself or else may be added as a dopant to the nematic phase, inducing the chiral nematic phase. This phenomenon was first investigated on cholesterol derivatives (eg. H. Baessler, M. M. Labes, *J. Chem. Phys.* 52, (1970) 631).

The chiral nematic phase has special optical properties: a high optical rotation and a pronounced circular dichroism resulting from selective reflection of circularly polarized light within the chiral nematic layer. Depending on the pitch of the helical superstructure it is possible to produce different colors which can appear different depending on the angle of view. The pitch of the helical superstructure depends in turn on the twisting power of the chiral component. In this case, it is possible, in particular by altering the concentration of a chiral dopant, to vary the pitch and hence the wavelength range of the selectively reflected light of a chiral nematic layer. Chiral nematic systems of this type have interesting possibilities for practical use.

Cholesteric special-effect pigments and compositions comprising such pigments are known.

EP-A-686 674 and its parent DE-A-44 16 191 describe interference pigments comprising molecules which are fixed in a cholesteric arrangement; the pigments feature a platelet-shaped structure and have, as one example demonstrates, a layer thickness of 7 μm. The pigments are prepared by applying highly viscous LC material to a substrate, the substrate being conveyed at a speed of about 2 m/min below a fixed doctor blade. By this means the liquid-crystalline molecules are oriented.

WO 97/30136 describes cholesteric polymer platelets which are obtainable from a chiral polymerizable mesogenic material. The platelets can be used as effect pigments. They are single-layered and have a preferred thickness of from 4 to 10 μm.

DE-A-196 39 179 discloses transparent compositions which comprise pigments whose coloredness is dependent on the viewing angle. The compositions are said to contain absorbtive colorants in an amount such that the angle-dependent color effect which occurs in the specular-angle configuration is intensified without any definite adverse effect on the transparency of the composition under all other angular configurations. The pigments are prepared as described in the abovementioned EP-A-686 674.

DE-A-196 39 229 discloses a composition in which at least one matrix, containing pigments whose coloredness is dependent on the viewing angle, is present in at least one further matrix in a two- or three-dimensionally structured format in the form of structural elements. These matrices 1 and 2 are non-identical, or contain non-identical pigments in identical concentrations. The pigments are prepared as described in the abovementioned EP-A-686 674.

DE-A-196 39 165 describes a method of obtaining new color effects by means of pigments whose coloredness depends on the viewing angle, in a matrix, where following their incorporation into the matrix the pigments are subjected to three- and/or two-dimensionally selective tilting in the matrix. The pigments are tilted preferably by means of differently directed movement of the pigments in the matrix or by using pigments differing in their concentration in the matrix. The pigments are prepared as described in the abovementioned EP-A-686 674.

DE-A-195 02 413 describes a pigment whose coloredness is dependent on the viewing angle and which has been obtained by three-dimensional crosslinking of oriented substances of liquid-crystalline structure with a chiral phase. In order to render such pigment colorfast with respect to elevated temperatures, it is proposed to conduct crosslinking in the presence of at least one additional, color-neutral compound which contains at least two crosslinkable double bonds. The uncrosslinked cholesteric mixture is applied by knife coating onto a film, for example. No details are given regarding the thickness of the layer applied by knife coating.

U.S. Pat. No. 5,364,557 describes cholesteric inks, for drawing and printing, which comprise platelet-shaped or flakelike cholesteric pigments. The pigments are prepared by coating a conveyor belt with a cholesteric melt and then smoothing and aligning the cholesteric film by means of a blade. The pigments can comprise two layers of different handedness or two layers of identical handedness with a further layer between them which inverts the direction of rotation of circularly polarized light. A light-absorbing layer is not described as a possible constituent of a layer pigment, especially since such a layer would work against the desired effect of 100% reflection of light.

U.S. Pat. No. 5,599,412 discloses a preparation process and apparatus for preparing cholesteric inks for writing and printing. Application and alignment of the melted polymer take place as described in the above-cited U.S. Pat. No. 5,364,557.

DE-A-44 18 076 describes effect coating materials and effect finishes which comprise interference pigments formed from esterified cellulose ethers. Using these interference pigments it is possible, it is said, to produce, in the case of the coating material, color changes which are dependent on the direction of incident light and on the direction of viewing, or to produce particularly intense hues of hitherto unknown brilliance on the article coated with such a material. The pigments are prepared by comminuting cholesteric layers which after curing are said to have a thickness of 5 to 200 μm. The layers are applied, for example by knife coating. In the examples, a layer thickness of approximately 10 μm is stated.

DE-A-196 297 61 describes cosmetic or pharmaceutical formulations which comprise pigments whose coloredness is dependent on the viewing angle. The pigments comprise at least one oriented crosslinked substance with a liquid-crystalline structure and with a chiral phase. The pigments are plateletlike in form and have a thickness of 1 to 20 μm. Preparation of the pigments is as described in the above-mentioned EP-A-686 674, although the layer thickness is said to be 5 μm rather than 7 μm.

Known from WO 96/02597 is a method of coating or printing substrates with a composition that comprises a chiral or achiral, liquid-crystalline monomer and a non-liquid-crystalline, chiral compound. The liquid-crystalline monomers are preferably photochemically polymerizable bisacrylates. To achieve the uniform orientation of the cholesteric phase, which is required for the development of the desired optical properties, and to achieve it even on large surfaces of complex form, it is necessary to add a polymeric binder. The layers, about whose thickness nothing is stated, are prepared via various printing techniques or by spraying.

DE-A-196 02 795 discloses a process for preparing pigment particles. The pigment particles have a substantially uniform, defined form and size, being prepared either by polymerizing a polymerizable mixture in uniformly dimensioned recesses or by initial shaping, by means of a printing process, and subsequent polymerization. The layer thickness of the pigments is not mentioned.

DE-A-196 02 848 describes a process for preparing pigments which employs a polymerizable mixture necessarily comprising, inter alia, a polymeric binder and/or monomeric compounds which can be converted by polymerization into a polymeric binder, and/or comprising a dispersing auxiliary. These auxiliaries are said to bring about a considerable improvement in the flow viscosity.

DE-A-42 40 743 discloses pigments whose coloredness is dependent on the viewing angle. The pigments are preferably prepared from three-dimensionally crosslinkable polyorganosiloxanes, the liquid-crystal mass being knife-coated onto a metal, plastic or glass substrate, crosslinked thermally or photochemically, and then the crosslinking product being detached from the substrate. The pigments preferably have a thickness of from 5 to 50 $\mu$m.

EP-B-383 376 describes liquid-crystal pigments comprising platelet-shaped carrier particles some of which at least are coated with liquid-crystalline material. Coating takes place by dispersing the platelet-shaped particles in a solvent in which liquid-crystalline material is dissolved, and then precipitating at least some of the liquid-crystalline material onto the particles. In the course of this the platelet-shaped carrier particles become fully or partly enveloped by the cholesteric. Uniform cholesteric layers arranged exactly parallel to the middle layer cannot be prepared by this process. The pigments are apparently not fully hiding, since they are said to be applied preferably to black surfaces.

DE-A-196 19 973 outlines, in a non-imitable manner, an idea for two- or three-layer platelet-shaped interference pigments. The pigments are intended to have at least one layer which consists of liquid-crystalline polymers whose mesogens are at least approximately in chiral-nematic and/or smectic and/or cholesteric order. Also provided in the interference pigments is a light-absorbing layer which is absorbent for at least part of the visible spectrum of light. The pigments are to be obtainable by knife coating, rolling or spray application to a smooth substrate, curing of the thin film thus produced, application of the light-absorbing layer, curing of this light-absorbing layer, optional application and curing of a further film which coincides with the first film in its composition and layer thickness, and removal and comminution of the cured layer assembly. Specific pigments, however, are not disclosed. As far as the material composition of the pigments is concerned, all that is said is that "liquid-crystalline main-chain or side-chain polymers or mixtures thereof, liquid-crystalline oligomers or oligomer mixtures, or liquid-crystalline monomers or monomer mixtures, [come] into consideration" as liquid-crystalline polymers. There are no examples regarding the preparation of the pigments or the pigment-containing coating formulations. The disclosure content of DE-A-196 19 973 is therefore limited to purely theoretical discussions of the idea of two- or three-layer pigments. Consequently, no technical teaching is provided that is imitable by the skilled worker.

WO 94/22976 and its parent GB-A 2276883 describe two-layer cholesteric pigments based on two different polyorganosiloxanes from the company Wacker. The pigments are prepared in an extremely complex manner by separate coating of two previously nylon-coated glass plates with solutions of the abovementioned liquid crystals; rubbing of each liquid-crystal layer in order to orient it; attachment of thermally deformable spacers to the glass plates; placing of the glass plates together with their cholesteric layers facing one another, and uniting of the cholesteric layers by thermal deformation of the spacers at elevated temperature in a vacuum, and also crosslinking of the united cholesteric layers. The film thus obtainable is said, like the pigments obtainable from it by milling, to have a thickness of approximately 10 $\mu$m. Despite the prior coating of the glass plates with nylon, detachment of the film from the glass plates is apparently incomplete, so that residues of the film have to be scraped off in order to obtain the pigments from the plates, which makes the preparation of the pigments even more complex. The idea of three-layer pigments is merely outlined. These pigments cannot be prepared by the preparation process described for two-layer pigments. Wo 94/22976 and its parent GB-A-2276883 therefore provide no technical teaching which is imitable by the skilled worker and which would in any way provide three-layer pigments. The disclosure content is limited to purely theoretical discussions of the structure of three-layer pigments.

In order to absorb the transmitting wavelength range, the prior interference pigments must either contain additional pigments in the cholesteric matrix or be applied to a colored background. When foreign pigments are incorporated into the liquid-crystalline mass it is disadvantageous that a considerable portion of the reflecting wavelength range is absorbed or scattered by absorption and scattered light, so that the special advantage of the interference pigments on a cholesteric basis is largely removed. The same problem occurs if cholesteric pigments are mixed with absorbing pigments into coating formulations. Reflections which disrupt the perceived color can only be avoided if the absorbing pigment is dispersed very finely into the cholesteric matrix. From general experience this is only the case if the pigment is dispersed using additives tailored specifically to the pigment surface. These compounds, such as fatty acids, salts of fatty acids, soya lecithins or phosphoric esters, however, interfere with the development of the helical orientation and this prevents optimum color development. If, on the other hand, absorption takes place over a colored underlayer, the background must be of uniformly high quality in order to provide the desired overall impression of the effect coating. Consequently, considerable effort has to be expended on pretreating the background. An ideal background for maximum brilliance would have to be black or have specular gloss, which in the case of car bodies, for example, would be extremely difficult to realize.

It is an object of the present invention to provide special-effect pigments which no longer have the above-described disadvantages of the prior art.

We have found that this object is achieved by a multi-layer pigment which comprises at least one layer which absorbs all or some transmitted light, installed between cholesteric layers.

The present invention therefore provides a platelet-shaped cholesteric multilayer pigment which comprises the layer sequence $A^1/B/A^2$ where $A^1$ and $A^2$ are identical or different and each comprise at least one cholesteric layer, and B is at least one interlayer which separates the layers $A^1$ and $A^2$ from one another and which absorbs all or some of the light transmitted by the layers $A^1$ and $A^2$.

The multilayer pigment of the invention offers a range of surprising advantages:

a) B can be made completely opaque (completely absorbing transmitted light) so that, with a sufficient level of pigmentation, the perceived color of the pigment is completely independent of the substrate and there is no need for the hitherto customary complex and costly tailoring of the substrate for transparent interference pigments. Self-opacifying cholesteric special-effect pigments are therefore provided for the first time.

b) The color of B can be varied, thereby providing a further control variable for the perceived color of the overall pigment.

c) The brightness of the overall pigment can additionally be adjusted by varying the gloss and/or roughness of B.

d) B can be tailored to the specific application in order to adjust the hardness and/or flexibility of the overall pigment.

e) B can be electrically conductive and is able thereby to impart electrical conductivity to the overall pigment without, in so doing, impairing the quality of the cholesteric layers.

f) $A^1$, B and $A^2$ are of uniform thickness and are stacked atop one another in parallel, hence forming a kind of sandwich structure which considerably increases the brightness of the pigment. This also brings about an improved perceived color in comparison with pigments having an all-round coating, since all of the cholesteric molecules of one layer have the same alignment.

g) The perceived color of the pigment is largely independent of external stimuli; in other words, it is stable over a wide range of temperature and pressure.

The top and the bottom cholesteric layer $A^1$ and $A^2$, respectively, of the pigment of the invention possess identical or different optical properties. They may, in particular, reflect light of the same or a different wavelength; in other words, they may be of the same or of a different color. In the latter case it is possible to achieve particularly interesting color effects. $A^1$ and $A^2$ are preferably different in their handedness, so that, for example, $A^1$ provides reflection of light of a certain wavelength in a left-handedly circular-polarized manner while $A^2$ reflects light of the same wavelength in a right-handedly circular-polarized manner. Advantageously, therefore, a paint comprising pigments of the invention in this preferred embodiment, for example, appears particularly bright since $A^1$ and $A^2$ in statistical distribution in the coat of paint face the incident light so that the coating reflects both right-handedly and left-handedly circular-polarized light of a certain wavelength, whereas a paint containing only pigments having just one cholesteric layer or having a plurality of cholesteric layers of the same handedness transmits either the left- or right-handedly circular-polarized light.

$A^1$ and $A^2$ can also be identical or different in terms of their mechanical properties. They may, for example, differ in thickness or brittleness.

B preferably comprises at least one organic or inorganic absorption pigment, preferably bound into a binder matrix. The absorption pigment can be a white, color or—preferably—black pigment. Examples of suitable inorganic absorption pigments are titanium dioxide, $Al_2O_3$, barium sulfate, strontium sulfate, zinc oxide, zinc phosphates, black iron oxide, lead chromate, strontium chromate, barium chromate and also metal pigments such as aluminum powder or bronze powder.

Examples of suitable organic absorption pigments are azo pigments, metal complex pigments, such as azo- and azomethine-metal complexes, isoindolinone and isoindoline pigments, phthalocyanine pigments, quinacridone pigments, perinone and perylene pigments, anthraquinone pigments, diketopyrrolopyrrole pigments, thioindigo pigments, dioxazine pigments, triphenylmethane pigments, quinophthalone pigments and fluorescent pigments.

Particularly suitable absorption pigments are fine such pigments having an average particle size of from 0.01 to 1 $\mu$m, preferably from 0.01 to 0.1 $\mu$m.

It is preferably possible to employ graphite pigments or various grades of carbon black, especially readily dispersible pigment-grade carbon blacks having a specific surface area of from 30 to 150 $m^2/g$ (BET method) and an absorption capacity of from 50 to 100 ml of dibutyl phthalate/100 g (DBP number).

Particularly preferred absorption pigments are those which impart magnetic properties to the layer B which absorbs transmitted light. Suitable examples are $\gamma$-$Fe_2O_3$, $Fe_3O_4$, $CrO_2$ or ferromagnetic: metal pigments, such as Fe, Fe—Cu and Fe—Ni—Co alloys, for example. With these pigments it is possible to produce highly lustrous black intermediate layers.

Pigments whose absorbing layer is magnetic can, advantageously, be given an arbitrary orientation by application of a magnetic field. In this way it is possible, for instance, to prevent individual pigment flakes projecting from the others, which results in the scattering of less light and an improvement in the perceived color. All of the flakes can be oriented together in a defined angle. It is also possible to generate full-area patterns for obtaining new color effects, or partial patterns for optical emphasis of letters or structures. The magnetic cholesteric pigments of the invention can also be employed with advantage in a liquid matrix, for example in LCDs, in which they alter their direction and therefore their perceived color when a magnetic field is applied.

The absorption pigments are preferably bound into an organic binder matrix. Suitable binders are the customary coatings systems. Suitable systems are preferably radiation-curable systems comprising reactive, crosslinkable groups, such as acrylic, methacrylic, $\alpha$-chloroacrylic, vinyl, vinyl ether, epoxy, cyanate, isocyanate or isothiocyanate groups.

Other binders which can be employed are monomeric agents and mixtures thereof with polymeric binders. Preferred monomeric agents are those which have two or more crosslinkable groups, such as acrylic, methacrylic, $\alpha$-chloroacrylic, vinyl, vinyl ether, epoxy, cyanate, isocyanate or isothiocyanate groups. Particular preference is given to acrylic, methacrylic or vinyl ether groups. Examples of monomeric agents having two crosslinkable groups are the diacrylates, the divinyl ethers or the dimethacrylates of diols such as propanediol, butanediol, hexanediol, ethylene glycol, diethylene glycol, triethylene glycol or tetrapropylene glycol, for example.

Examples of monomeric agents having three crosslinkable groups are the triacrylates, the trivinyl ethers or the trimethacrylates of triols such as trimethylolpropane, ethoxylated trimethylolpropane having 1 to 20 ethylene oxide units, propoxylated trimethylolpropane having 1 to 20 propylene oxide units, and mixed ethoxylated and propoxylated trimethylolpropane in which the sum of ethylene oxide and propylene oxide units is from 1 to 20. Examples of monomeric agents having three crosslinkable groups are also the triacrylates the trivinyl ethers or the trimethacrylates of glycerol, ethoxylated glycerol having 1 to 20 ethylene oxide units, propoxylated glycerol having 1 to 20 propylene oxide units, and mixed ethoxylated and propoxylated glycerol in which the sum of ethylene oxide and propylene oxide units is from 1 to 20.

Examples of monomeric agents having four crosslinkable groups are the tetraacrylates, the tetravinyl ethers or the tetramethacrylates of tetraols such as bis-trimethylolpropane, ethoxylated bis-trimethylolpropane having 1 to 20 ethylene oxide units, propoxylated bis-trimethylolpropane having 1 to 20 propylene oxide units, and mixed ethoxylated and propoxylated bis-trimethylolpropane, in which the sum of ethylene oxide and propylene oxide units is from 1 to 20. Further examples of monomeric agents having four crosslinkable groups are the tetraacrylates, the tetravinyl ethers or the tetramethacrylates of tetraols such as pentaerythritol, ethoxylated pentaerythritol having 1 to 20 ethylene oxide units, propoxylated pentaerythritol having 1 to 20 propylene oxide units, and mixed ethoxylated and propoxylated pentaerythritol in which the sum of ethylene oxide and propylene oxide units is from 1 to 20.

To enhance the reactivity in the course of crosslinking or polymerization in air it is possible for the binders and the monomeric agents to include from 0.1 to 10% of a primary or secondary amine. Examples of suitable amines are ethanolamine, diethanolamine or dibutylamine.

With particular preference, the absorption pigments of the layer B are bound into a binder matrix which comprises the cholesteric mixtures described further below as constituents of the layers $A^1$ and $A^2$. With very particular preference, the binder matrix of the layer B comprises the same cholesteric mixtures as the layers $A^1$ and $A^2$.

The absorption pigment formulation can be prepared by the customary dispersion techniques, which are known in the art, and using diluents, dispersants, photoinitiators and, if desired, further additives.

Diluents which can be used are water or organic liquids or mixtures thereof, preference being given to organic liquids. Particularly preferred organic liquids are those having a boiling point of below 140° C., especially ethers such as tetrahydrofuran, ketones such as ethyl methyl ketone and esters such as butyl acetate.

Dispersants which can be used are low molecular mass dispersants such as stearic acid, for example, or else polymeric dispersants. Suitable polymeric dispersants or dispersing resins are known to the skilled worker. Particular mention may be made of sulfonate-, phosphate-, phosphonate- or carboxyl-functional polyurethanes, carboxyl-functional vinyl chloride copolymers, polyimine polyesters or polyether acrylates with or without incorporated functional groups.

For the preparation of crosslinkable or polymerizable absorption pigment formulations it is possible to use the photoinitiators customary for photochemical polymerization, examples being the photoinitiators listed below for the photochemical polymerization of the cholesteric mixtures.

The thickness of each individual cholesteric layer of $A^1$ or $A^2$ is preferably from about 0.5 to 20 μm, in particular from about 1 to 10 μm and, with particular preference, from about 2 to 4 μm. The thickness of each individual layer of B is from about 0.2 to 5 μm, in particular from about 0.5 to 3 μn. The diameter of the pigments of the invention is from about 5 to 500 μm, in particular from about 10 to 100 μm and, with particular preference, from about 10 to 30 μm. In general the pigment diameter is approximately 5 times the pigment thickness.

$A^1$ and $A^2$ of the pigments of the invention preferably comprise cholesteric mixtures selected from a) at least one cholesteric, polymerizable monomer;

b) at least one achiral, nematic, polymerizable monomer and one chiral compound;

c) at least one cholesteric, crosslinkable oligomer or polymer; or d) a cholesteric polymer in a polymerizable diluent;

e) at least one cholesteric polymer whose cholesteric phase can be frozen in by rapid cooling to below the glass transition temperature, in the cured state.

Curing fixes the uniform orientation of the cholesteric molecules in the cholesteric layer.

Preferred monomers of group a) are described in DE-A-196 02 848, the full content of which is incorporated herein by reference. In particular, the monomers a) embrace at least one chiral, liquid-crystalline, polymerizable monomer of the formula I $$[Z^1\text{—}Y^1\text{—}A^1\text{—}Y^2\text{—}M^1\text{—}Y^3\text{—}]_n\ X \qquad (I)$$

where $Z^1$ is a polymerizable group or a radical which carries a polymerizable group, $Y^1, Y^2, Y^3$ independently are chemical bonds, oxygen, sulfur, —CO—O—, —O—CO—, —O—CO—O—, —CO—N(R)— or —N(R)—CO—, $A^1$ is a spacer, $M^1$ is a mesogenic group, X is an n-valent chiral radical, R is hydrogen or $C_1$–$C_4$-alkyl, n is 1 to 6, and $Z^1, Y^1, Y^2, Y^3, A^1$ and $M^1$ can be identical or different if n is greater than 1.

Preferred radicals $Z^1$ are:

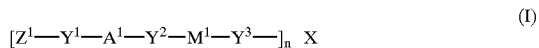

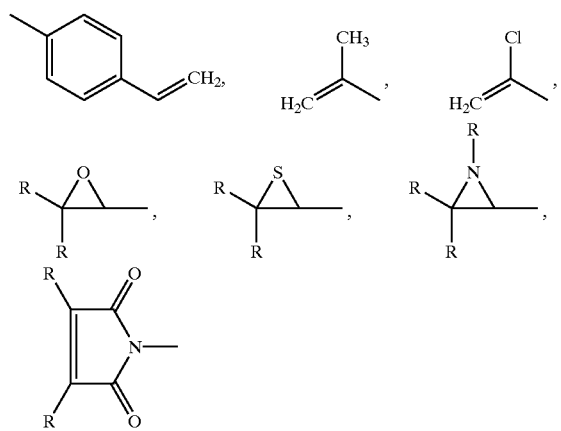

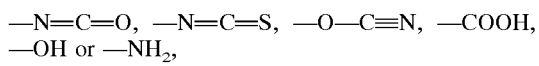

where each R can be identical or different and is hydrogen or $C_1$–$C_4$-alkyl, such as methyl, ethyl, n-propyl, isopropyl, n-butyl, isobutyl, sec-butyl or tert-butyl. Of the reactive polymerizable groups, the cyanates are able to trimerize spontaneously to cyanurates and are therefore preferred. Polymerization of the other groups indicated requires further compounds having complementary reactive groups. Isocyanates, for example, are able to polymerize with alcohols to give urethanes and with amines to give urea derivatives. Similar comments apply to thiiranes and aziridines. Carboxyl groups can be condensed to give polyesters and polyamides. The maleimido group is particularly suitable for free-radical copolymerization with olefinic compounds such as styrene. Said complementary reactive groups can be present either in a second compound of the invention, which is mixed with the first, or can be incorporated into the polymeric network by means of auxiliary compounds containing 2 or more such complementary groups.

Particularly preferred groups $Z^1$–$Y^1$ are acrylate and methacrylate. $Y^1$–$Y^3$ can be as defined above, the term a chemical bond meaning a single covalent bond.

Suitable spacers $A^1$ are all groups known for this purpose. The spacers contain generally 1 or more, for example from 2 to 30, preferably 1 to 12 or 2 to 12 carbons and consist of linear aliphatic groups. They may be interrupted in the chain by nonadjacent O, S, NH or $NCH_3$, for example. Other suitable substituents for the spacer chain are fluorine, chlorine, bromine, cyano, methyl and ethyl.

Examples of representative spacers are:

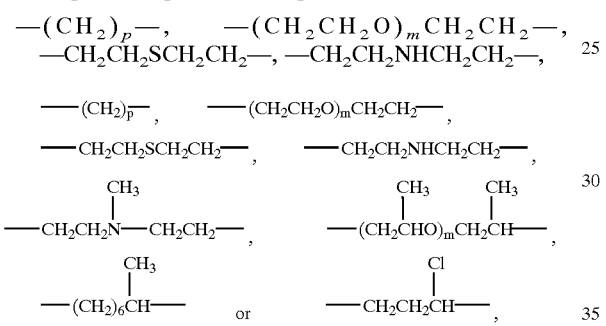

where m is 1 to 3 and p is 1 to 12.

The mesogenic group $M^1$ preferably has the structure $(T-Y^8)_s-T$ where $Y^8$ is a bridge in accordance with one of the definitions of $Y^1$, s is 1 to 3 and T is identical or different at each occurrence and is a divalent isocycloaliphatic, heterocycloaliphatic, isoaromatic or heteroaromatic radical.

The radicals T can also be ring systems substituted by $C_1$–$C_4$-alkyl, fluorine, chlorine, bromine, cyano, hydroxyl or nitro. Preferred radicals T are:

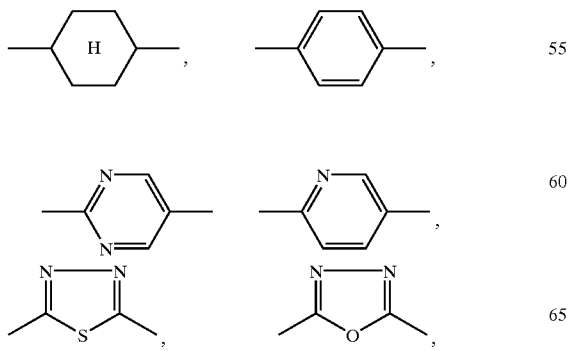

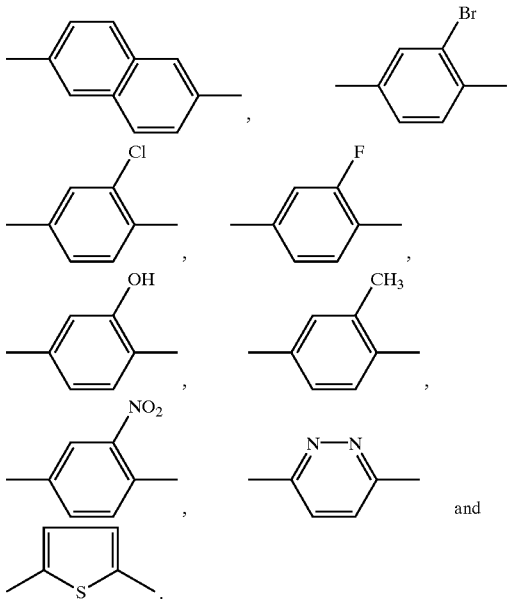

Particular preference is given to the following mesogenic groups $M^1$:

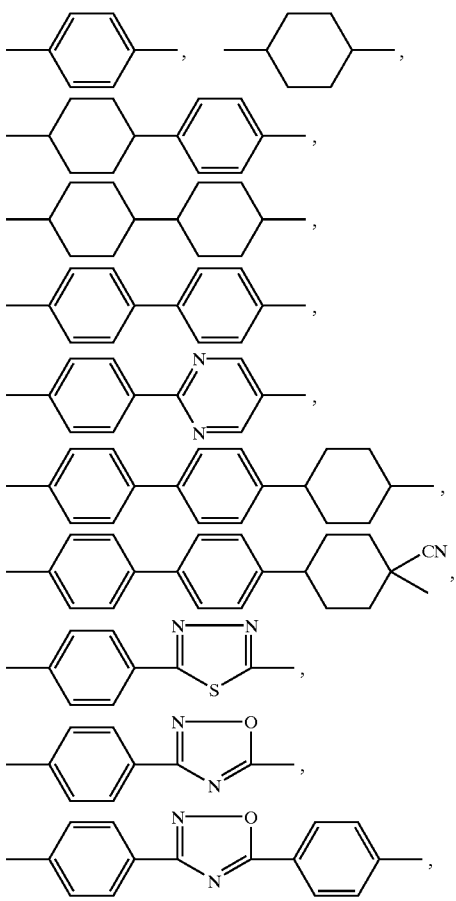

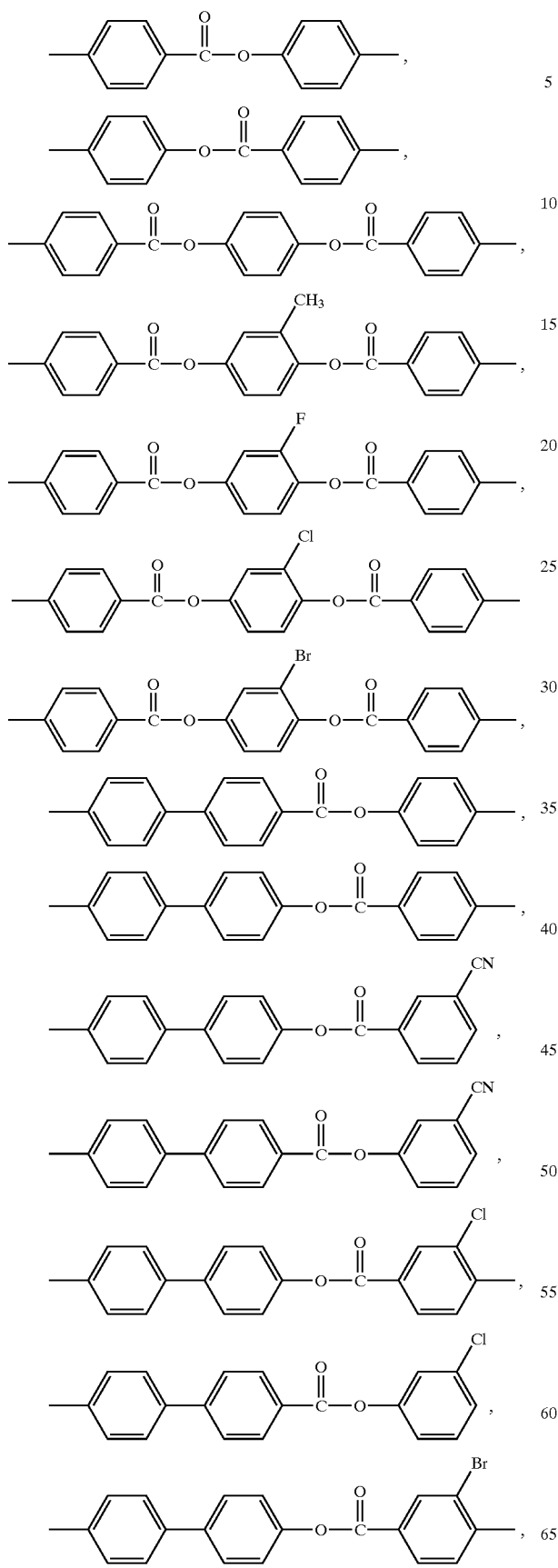

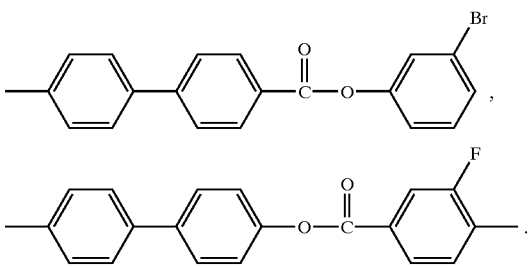

Of the chiral radicals X of the compounds of the formula I particular preference is given, partly on account of their availability, to those derived from sugars, from binaphthyl or biphenyl derivatives and from optically active glycols, dialcohols or amino acids. In the case of the sugars, particular mention should be made of pentoses and hexoses and derivatives thereof.

Examples of radicals X are the following structures, the lines at the end in each case denoting the free valences.

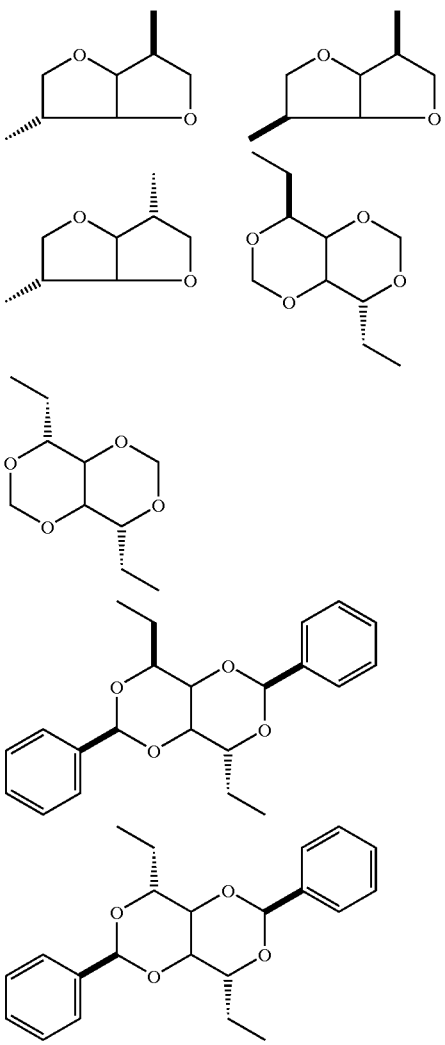

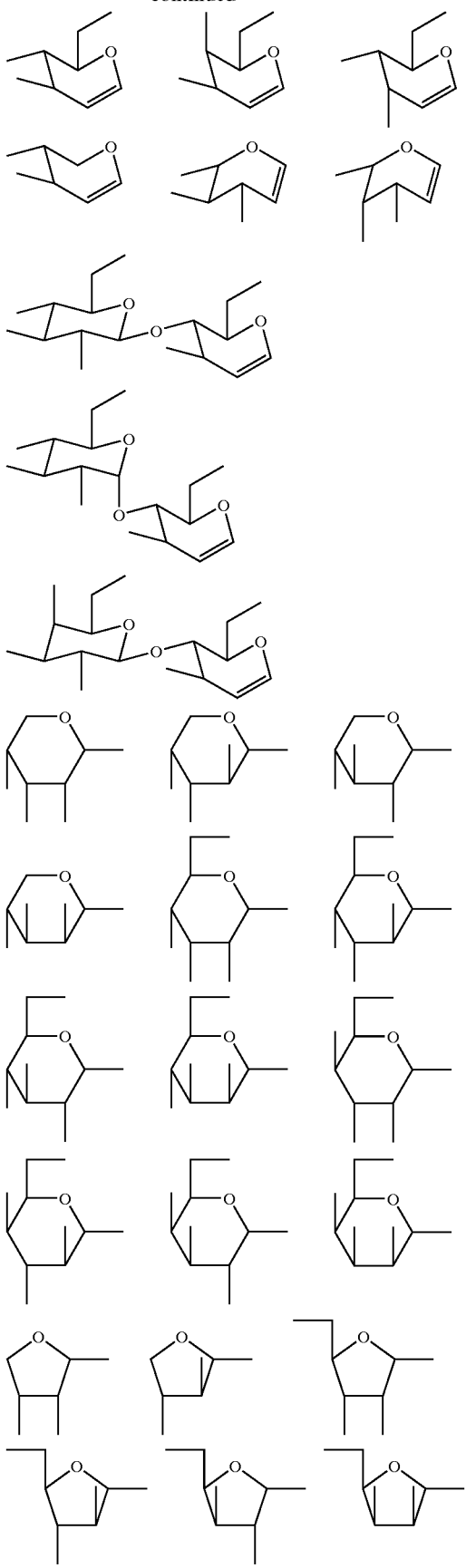
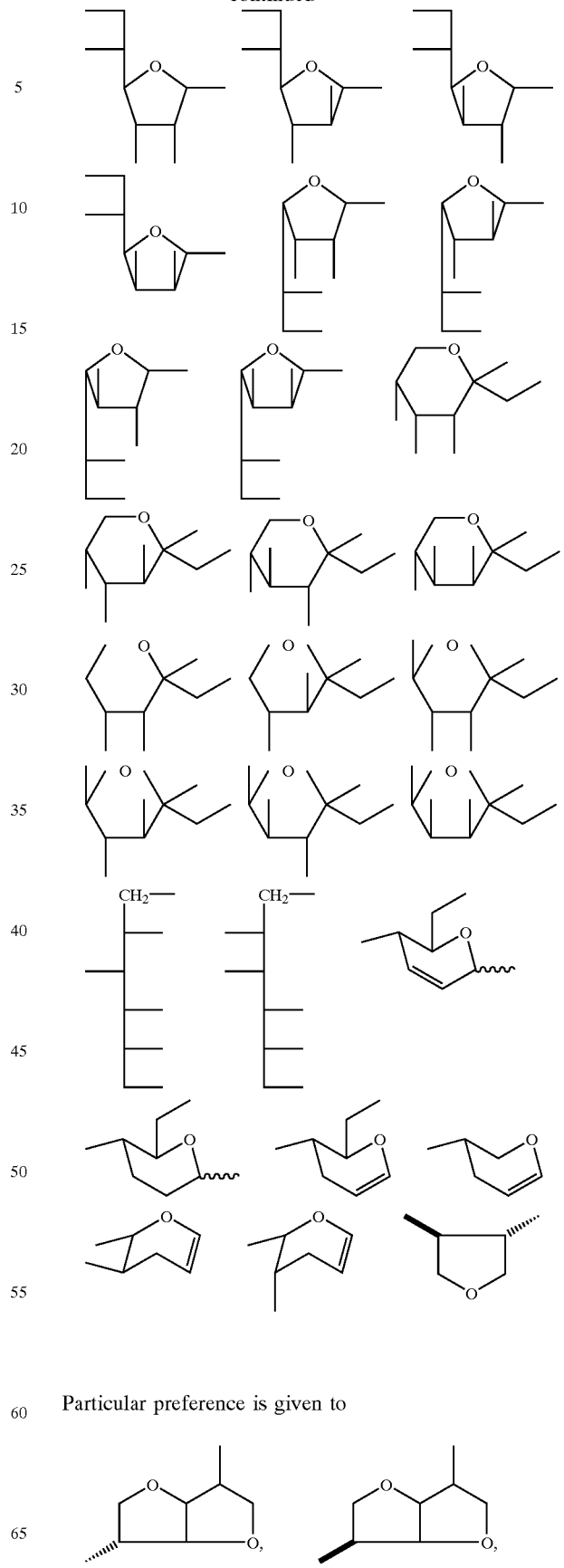
Particular preference is given to
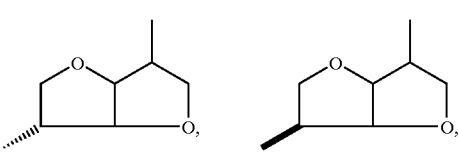

-continued

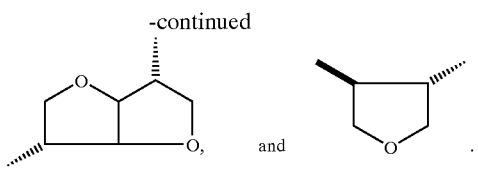
and

Also suitable, furthermore, are chiral groups having the following structures:

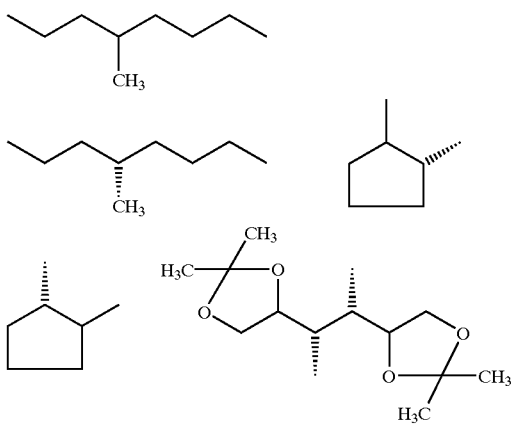

Further examples are set out in the German Application P 43 42 280.2.

n is preferably 2.

As preferred monomers of group b), the cholesteric mixture in the process of the invention includes at least one achiral liquid-crystalline polymerizable monomer of the formula II $$Z^2{-}Y^4{-}A^2{-}Y^5{-}M^2{-}Y^6{-}A^3{-}Y^7{-}Z^3)_n \qquad (II)$$

where $Z^2$, $Z^3$ are identical or different polymerizable groups or radicals which contain a polymerizable group, n is 0 or 1, $Y^4$, $Y^5$, $Y^6$, $Y^7$ independently are chemical bonds, oxygen, sulfur, —CO—O—,—O—CO—O—CO—O—, —CO—N(R)— or —N(R)—CO—, $A^2$, $A^3$ are identical or different spacers and $M^2$ is a mesogenic group.

The polymerizable groups, bridges $Y^4$ to $Y^7$, the spacers and the mesogenic groups are subject to the same preferences as the corresponding variables of the formula I.

In addition, the mixture of group b) includes a chiral compound. The chiral compound brings about the twisting of the achiral liquid-crystalline phase to form a cholesteric phase. In this context, the extent of twisting depends on the twisting power of the chiral dopant and on its concentration. Consequently, therefore, the pitch of the helix and, in turn, the interference color depend on the concentration of the chiral dopant. As a result, it is not possible to indicate a generally valid concentration range for the dopant. The dopant is added in the amount at which the desired color effect is produced.

Preferred chiral compounds are those of the formula Ia $$[Z^1{-}Y^1{-}A^1{-}Y^2{-}M^a{-}Y^3{-}]_n \, X, \qquad (Ia)$$

where $Z^1$, $Y^1$, $Y^2$, $Y^3$, $A^1$, X and n are as defined above and $M^a$ is a divalent radical which comprises at least one heterocyclic or isocyclic ring system.

The moiety $M^a$ here is similar to the mesogenic groups described, since in this way particularly good compatibility with the liquid-crystalline compound is achieved. Ma, however, need not be mesogenic, since the compound Ia is intended merely by means of its chiral structure to bring about the appropriate twisting of the liquid-crystalline phase. Preferred ring systems present in $M^a$ are the abovementioned structures T, preferred structures $M^a$ being those of the abovementioned formula $(T{-}Y^8)_s{-}T$. Further monomers and chiral compounds of group b) are described in WO 97/00600 and its parent DE-A-195 324 08, the full content of which is expressly incorporated herein by reference.

Preferred polymers of group c) are cholesteric cellulose derivatives as described in DE-A-197 136 38, especially cholesteric mixed esters of (VI) hydroxyalkyl ethers of cellulose with (VII) saturated, aliphatic or aromatic carboxylic acids and (VIII) unsaturated mono- or dicarboxylic acids.

Particular preference is given to mixed esters in which the hydroxyalkyl radicals of component VI that are attached by way of ether functions are straight-chain or branched $C_2$–$C_{10}$-hydroxyalkyl radicals, especially hydroxypropyl and/or hydroxyethyl radicals. Component VI of the mixed esters of the invention preferably has a molecular weight of from about 500 to about 1 million. Preferably, the anhydroglucose units of the cellulose are etherified with hydroxyalkyl radicals in an average molar degree of substitution of from 2 to 4. The hydroxyalkyl groups in the cellulose can be identical or different. Up to 50% of them can also be replaced by alkyl groups (especially $C_1$–$C_{10}$-alkyl groups). One example of such a compound is hydroxypropylmethylcellulose.

Compounds which can be used as component VII of the mixed esters that are employable are straight-chain aliphatic $C_1$–$C_{10}$ carboxylic acids, especially $C_2$–$C_6$ carboxylic acids, branched aliphatic $C_4$–$C_{10}$ carboxylic acids, especially $C_4$–$C_6$ carboxylic acids, or straight-chain or branched halocarboxylic acids. Component VII can also comprise benzoic acid or aliphatic carboxylic acids with aromatic substituents, especially phenylacetic acid. Component VII is with particular preference selected from acetic, propionic, n-butyric, isobutyric and n-valeric acid, in particular from propionic, 3-chloropropionic, n-butyric and isobutyric acid.

Component VIII is preferably selected from unsaturated $C_3$–$C_{12}$ mono- or dicarboxylic acids or monoesters of such dicarboxylic acids, especially from α,β-ethylenically unsaturated $C_3$–$C_6$ mono- or dicarboxylic acids or monoesters of the dicarboxylic acids.

Component VIII of the mixed esters that are employable is with particular preference selected from acrylic, methacrylic, crotonic, vinylacetic, maleic, fumaric and undecenoic acid, especially from acrylic and methacrylic acid.

Component VI is preferably esterified with component VII and VIII in an average molar degree of substitution of from 1.5 to 3, in particular from 1.6 to 2.7 and, with particular preference, from 2.3 to 2.6. Preferably about 1 to 30%, in particular from 1 to 20% or 1 to 10% and, with particular preference, from about 5 to 7% of the OH groups of component VI are esterified with component VIII.

The proportion of component VII to component VIII determines the hue of the polymer.

Highly suitable polymers of group c), moreover, are the propargyl-terminated cholesteric polyesters or polycarbonates described in DE-A-197 17 371.

It is also possible to employ crosslinkable oligo- or polyorganosiloxanes, as are known, for example, from EP-A-0 358 208, DE-A-195 41 820 or DE-A-196 19 460.

Among these compounds preference is given to polyesters or polycarbonates having at least one propargyl end group of the formula $R^3C\equiv C-CH_2-$, where $R^3$ is H, $C_1-C_4$-alkyl, aryl or $Ar-C_1-C_4$-alkyl (eg. benzyl or phenethyl) and which is attached to the polyesters or polycarbonates directly or via a linker. The linker is preferably selected from $-O-$, $-S-$, $-NR^4-$,

(the propargyl group is attached to X), where $R^4$ is H, $C_1-C_4$-alkyl or phehyl, X is O, S or $NR^2$ and $R^2$ is H, $C_1-C_4$-alkyl or phenyl.

In the polyesters, the propargyl end group is preferably attached by way of

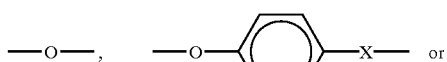

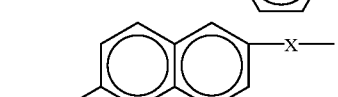

(X = O, S)

The polyesters preferably comprise (IX) at least one aromatic or araliphatic dicarboxylic acid unit and/or at least one aromatic or araliphatic hydroxycarboxylic acid unit, and (X) at least one diol unit.

Preferred dicarboxylic acid units are those of the formula

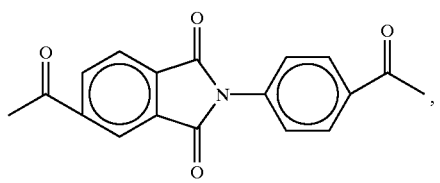

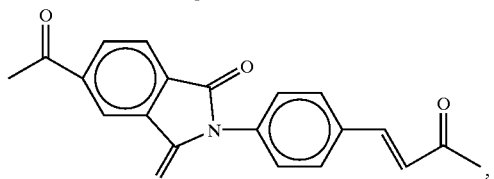

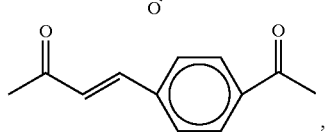

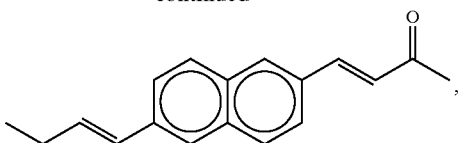

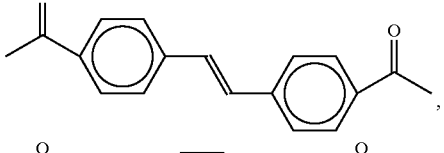

especially those of the formula

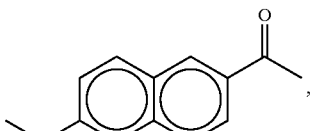

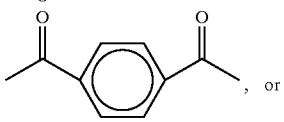

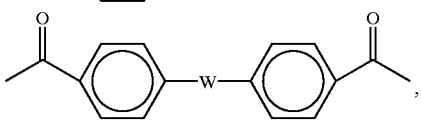

where each of the phenyls or the naphthyl can carry 1, 2 or 3 substituents selected independently from $C_1-C_4$-alkyl, $C_1-C_4$-alkoxy, halogen or phehyl, and where W is NR, S, O, $(CH_2)_pO(CH_2)_q$, $(CH_2)_m$ or a single bond, R is alkyl or hydrogen, m is an integer from 1 to 15, and p and q independently are integers from 0 to 10.

Preferred hydroxycarboxylic acid units are those of the formula

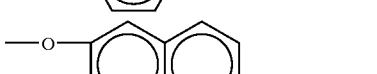

where each phenyl or the naphthyl can carry 1, 2 or 3 substituents selected independently from $C_1-C_4$-alkyl, $C_1-C_4$-alkoxy, halogen or phenyl.

Preferred diol units are those of the formula

[chemical structures]

especially those of the formula

[chemical structures]

where

L is alkyl, alkoxy, halogen, COOR, OCOR, CONHR or NHCOR,

X is S, O, N, $CH_2$ or a single bond,

A is a single bond, $(CH_2)_n$, $O(CH_2)_n$, $S(CH_2)_n$, $NR(CH_2)_n$,

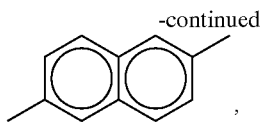,

R is alkyl or hydrogen,
R¹ is hydrogen, halogen, alkyl or phehyl, and
n is an integer from 1 to 15.

Preference is given to polyesters comprising at least one dicarboxylic acid unit of the formula

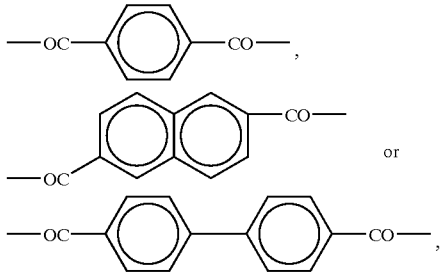

and at least one diol unit of the formula

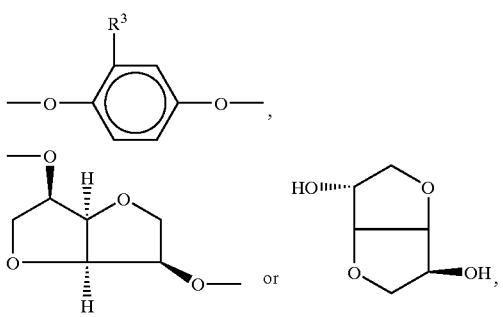

where $R^3$ is H, halogen, $C_1$–$C_4$-alkyl, especially $CH_3$ or $C(CH_3)_3$, or is phenyl.

Further preferred compounds are diesters of the formula P—Y—B—CO—O—A—O—CO—B—Y—P, where P is a propargyl end group of the above-defined formula, Y is O, S or $NR^2$ ($R^2$=$C_1$–$C_4$-alkyl), B is

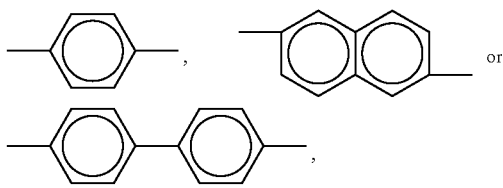

where each phenyl or the naphthyl can carry 1, 2 or 3 substituents selected independently from $C_1$–$C_4$-alkyl, $C_1$–$C_4$-alkoxy, halogen or phehyl, and A (together with the adjacent oxygens) is one of the abovementioned diol units.

Particularly preferred diesters are those of the above formula in which B is

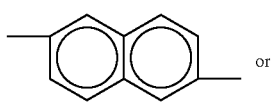 or

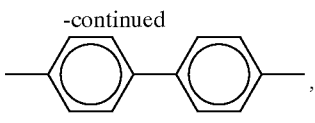, and especially diesters of the formula

HC≡CCH₂O—B—CO—O—A—O—CO—B—OCH₂—C≡CH,
where (XI) B is  and

A is 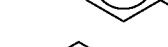, ,

, ,

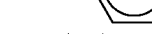,  or (XII) B is 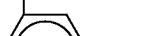, and

A is as defined under XI.

Further preferred compounds are polycarbonates comprising at least one incorporated diol unit of the above formulae, especially of the formulae

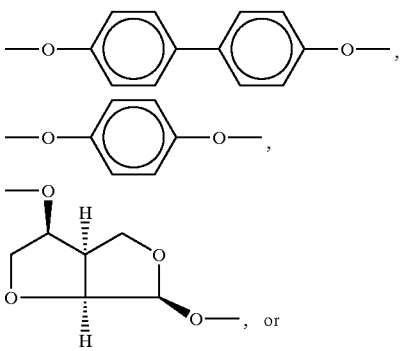

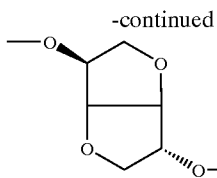

Preference is given here to those polycarbonates which comprise as diol units at least one mesogenic unit of the formula

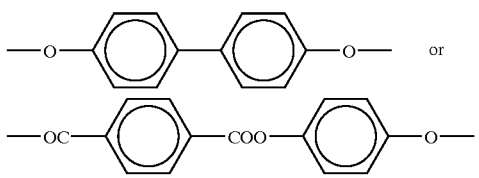

and at least one chiral unit of the formula

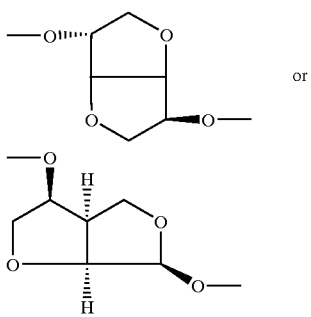

and, if desired, a nonchiral unit of the formula

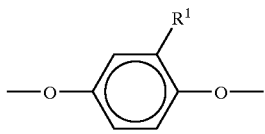

where $R^1$ is as defined above and in particular is H or $CH_3$.

Particularly preferred polycarbonates are those having propargyl end groups of the formula $HC\equiv CCH_2O-R^5-CO$, in which $R^5$ is

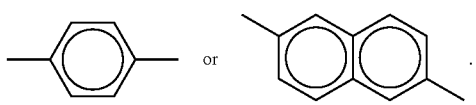

Further suitable polymers of group c) are cholesteric polycarbonates containing photoreactive groups even in a nonterminal position. Such polycarbonates are described in DE-A-196 31 658 and are preferably of the formula XIII where the molar ratio w/x/y/z is from about 1 to 20/from about 1 to 5/from about 0 to 10/from about 0 to 10. Particular preference is given to a molar ratio w/x/y/z of from about 1 to 5/from about 1 to 2/from about 0 to 5/from about 0 to 5.

In the formula XIII

A is a mesogenic group of the formula

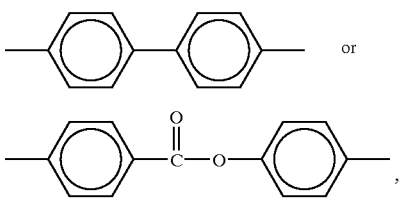

B is a chiral group of the formula

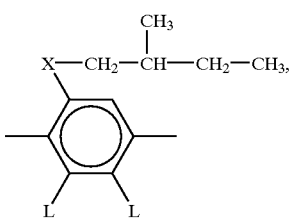

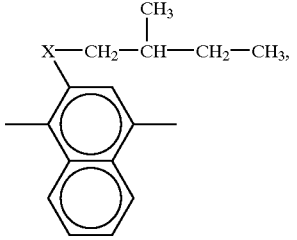

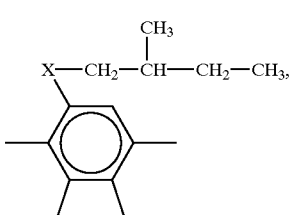

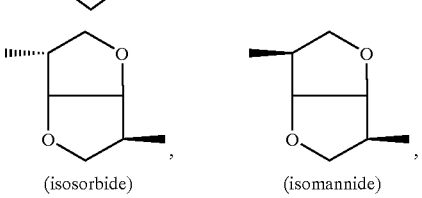

(isosorbide)   (isomannide)

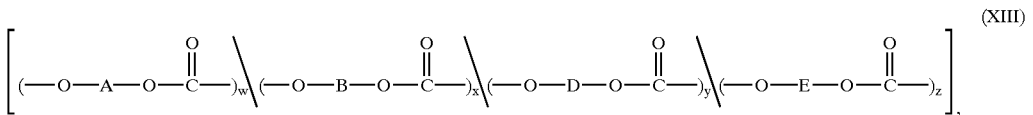

(XIII)

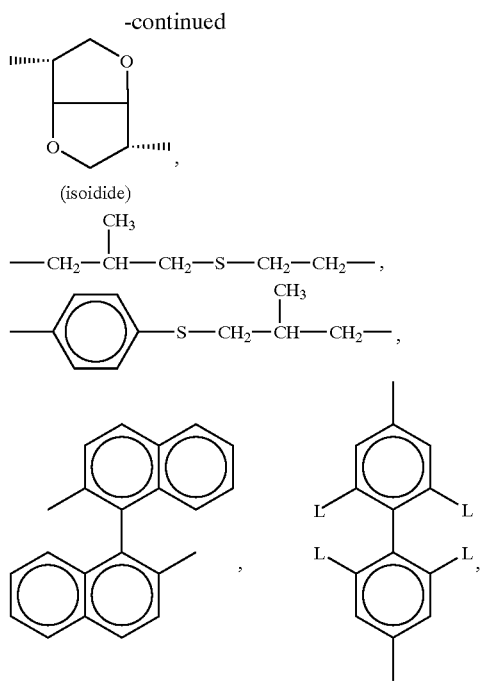

(isoidide),

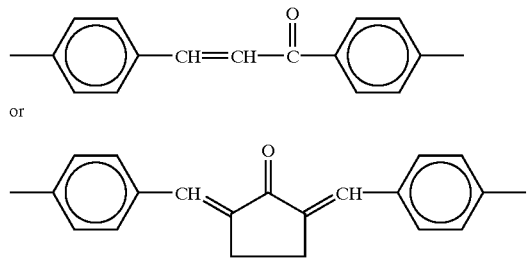

D is a photoreactive group of the formula

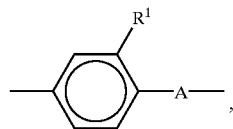

or

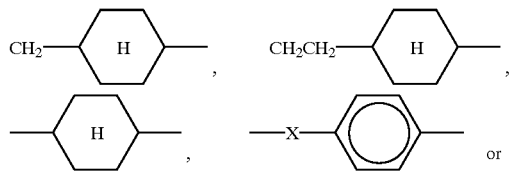

and

E is a further, nonchiral group of the formula

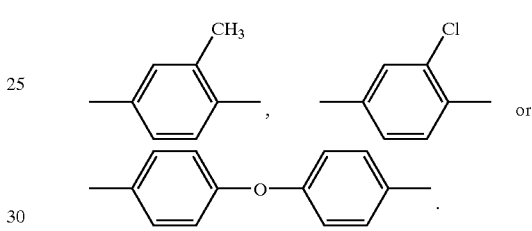

where

L is alkyl, alkoxy, halogen, COOR, OCOR, CONHR or NHCOR,

X is S, O, N, $CH_2$ or a single bond,

R is alkyl or hydrogen,

A is a single bond, $(CH_2)_n$, $O(CH_2)_n$, $S(Cu_2)_n$, $NR(CH_2)_n$,

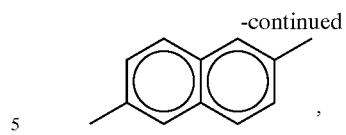

,

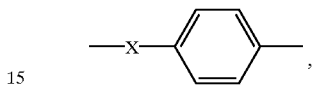

$R^1$ is hydrogen, halogen, alkyl or phehyl, and n is an integer from 1 to 15.

If $R^1$ is alkyl or halogen and A is a single bond or if $R^1$ is H or alkyl and A is

,

—$O(CH_2)_n$—, —$S(CH_2)_n$ or —$NR(CH_2)_n$ the groups concerned are solubility-enhancing groups. Examples of these are Isosorbide, isomannide and/or isoidide is the preferred chiral component.

The proportion of the chiral diol structural units is preferably within the range from 1 to 80 mol-% of the overall content of diol structural units, with particular preference from 2 to 20 mol-%, depending on the desired interference hue.

Suitable polymers of group e) are chiral nematic polyesters having flexible chains and comprising isosorbide, isomannide and/or isoidide units, preferably isosorbide units, and also comprising at least one chain-flexibilizing unit selected from (and derived from)

(a) aliphatic dicarboxylic acids, (b) aromatic dicarboxylic acids with a flexible spacer, (c) α,ω-alkanoids, (d) diphenols with a flexible spacer, and (e) condensation products of a polyalkylene terephthalate or polyalkylene naphthalate with an acylated diphenol and with an acylated isosorbide, as are described in DE-A-197 04 506.

The polyesters are noncrystalline and form stable Grandjean textures which can be frozen in on cooling to below the glass transition temperature. The glass transition temperatures of the polyesters are in turn, despite the flexibilization, above 80° C., preferably above 90° C. and, in particular, above 100° C.

The polyesters that can be employed include as units (a) preferably those of the formula —OC—$(CH_2)_n$—CO— where n is from 3 to 15, especially 4 to 12, and with particular preference adipic acid;

as units (b) preferably those of the formula

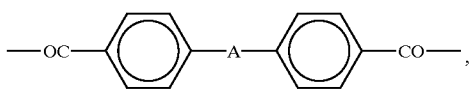

where

A is $(CH_2)_n$, $O(CH_2)_nO$ or $(CH_2)_o$—O—$(CH_2)_p$,
n is from 3 to 15, especially 4 to 12, with particular preference 4 to 10, and
o and p independently are from 1 to 7;

as units (c) preferably those of the formula

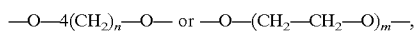

where n is from 3 to 15, especially 4 to 12, with particular preference 4 to 10, and
m is from 1 to 10; and as units (d) preferably those of the formula

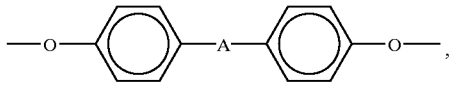

where

A is $(CH_2)_n$, $O(CH_2)_nO$ or $(CH_2)_o$—O—$(CH_2)_p$,
n is from 3 to 15, especially 4 to 12, with particular preference 4 to 10, and
o and p independently are from 1 to 7.

The polyesters that can be employed additionally comprise, as nonflexible acid component, preferably dicarboxylic acid units of the formula

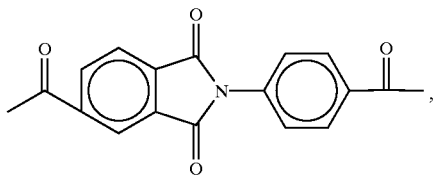

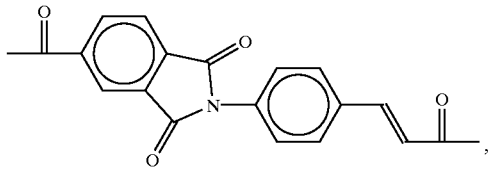

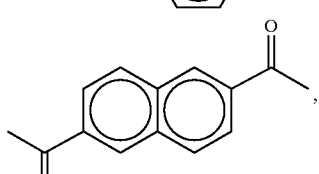

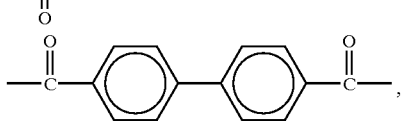

-continued

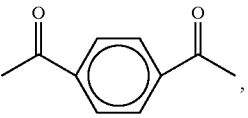

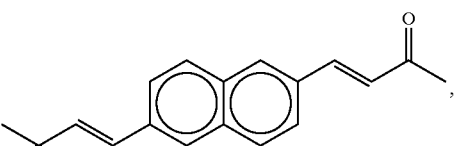

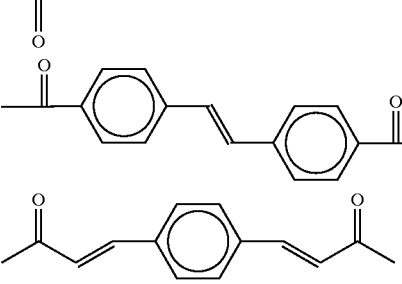

or and as nonflexible alcohol component diol units of the formula

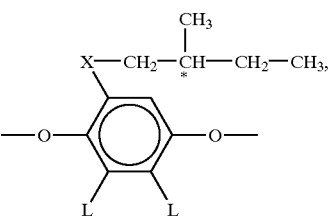

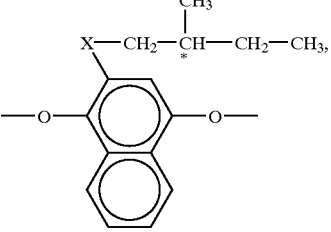

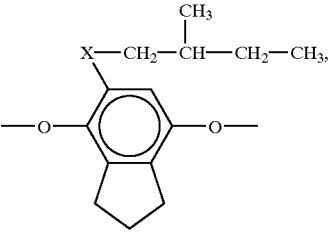

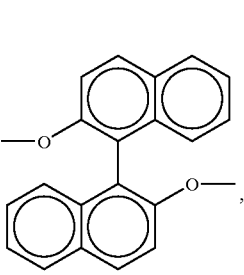

-continued

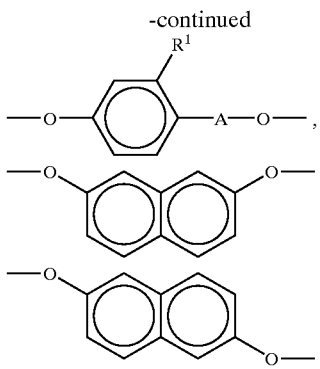

where

L is alkyl, alkoxy, halogen, COOR, OCOR, CONHR or NHCOR,

X is S, O, N, CH$_2$ or a single bond,

A is a single bond,

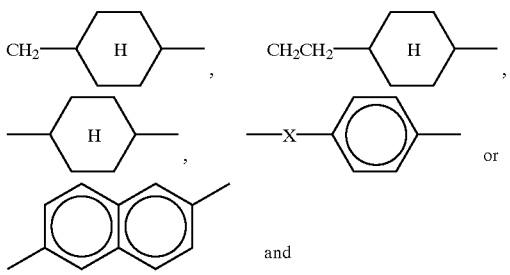

where

R$^1$ is hydrogen, halogen, alkyl or phenyl and

R is alkyl or hydrogen.

If desired, the polyesters that can be employed comprise additional flexible diol units of the formula

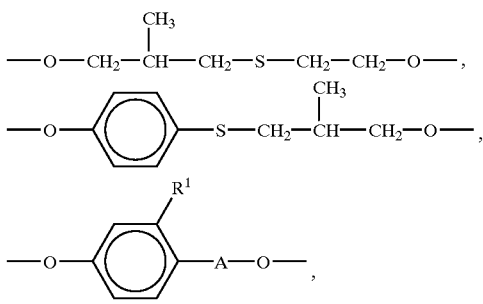

where

R$^1$ is hydrogen, halogen, alkyl or phehyl,

A is (CH$_2$)$_n$, O(CH$_2$)$_n$, S(CH$_2$)$_n$ or NR(CH$_2$)$_n$, and n is from 1 to 15.

Examples of preferred polymers of group d) are crosslinkable cholesteric copolyisocyanates as described in U.S. Pat. No. 8,834,745. Such copolyisocyanates feature repeating units of the formulae

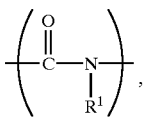
(III)

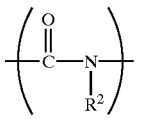
(IV)

and if desired of the formula

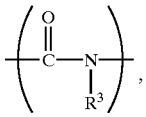
(V)

where

R$^1$ is a chiral aliphatic or aromatic radical,

R$^2$ is a crosslinkable radical and

R$^3$ is an achiral radical.

Unless stated otherwise, alkyl is to be understood here (both alone and in definitions such as alkoxy, dialkyl, alkylthio, etc.) as branched and unbranched C$_1$–C$_{12}$-alkyl, preferably C$_3$–C$_{12}$—, with particular preference C$_4$–C$_{10}$- and, in particular, C$_6$–C$_{10}$-alkyl.

R$^1$ is preferably selected from (chiral) branched or unbranched alkyl, alkoxyalkyl, alkylthioalkyl, cycloalkyl, alkylphenyl or C$_3$–C$_9$-epoxyalkyl radicals or radicals from esters of C$_1$–C$_6$ fatty acids with C$_1$–C$_6$-alkanols or C$_3$–C$_9$-dialkyl ketones. The ester radical may be attached to the nitrogen either via the fatty acid moiety or via the alkanol residue. The radical R$^1$ may have 1, 2 or 3 substituents, which are identical or different and are selected from alkoxy, di-C$_1$–C$_4$-alkylamino, CN or C$_1$–C$_4$-alkylthio groups or halogen atoms.

R$^1$ is preferably selected from alkyl, alkoxyalkyl, radicals from esters of C$_1$–C$_6$ fatty acids with C$_1$–C$_6$-alkanols, C$_3$–C$_9$-dialkyl ketones and epoxidized C$_3$–C$_9$-epoxyalkyl radicals, where R$^1$ may be substituted by 1 or 2 radicals which are identical or different and are selected from alkoxy, halogen, CN and CF$_3$. Preferred substituents of branched or unbranched alkyl or alkoxy radicals are selected from alkoxy groups, halogen atoms and CN; for esters of C$_1$–C$_6$ fatty acids with C$_1$–C$_6$-alkanols, from alkoxy groups, halogen atoms, CN and CF$_3$; and, for C$_3$–C$_9$-dialkyl ketones, from alkoxy groups, halogen atoms and CN.

The main chain of the radical R$^1$ has, in particular, a length of from 3 to 12, especially 6 to 10, preferably 6 to 8 members (carbons, oxygens and/or sulfurs). Particularly preferred radicals R$^1$ are selected from

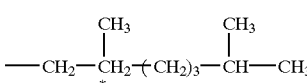

2,6-dimethylheptyl

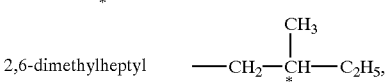

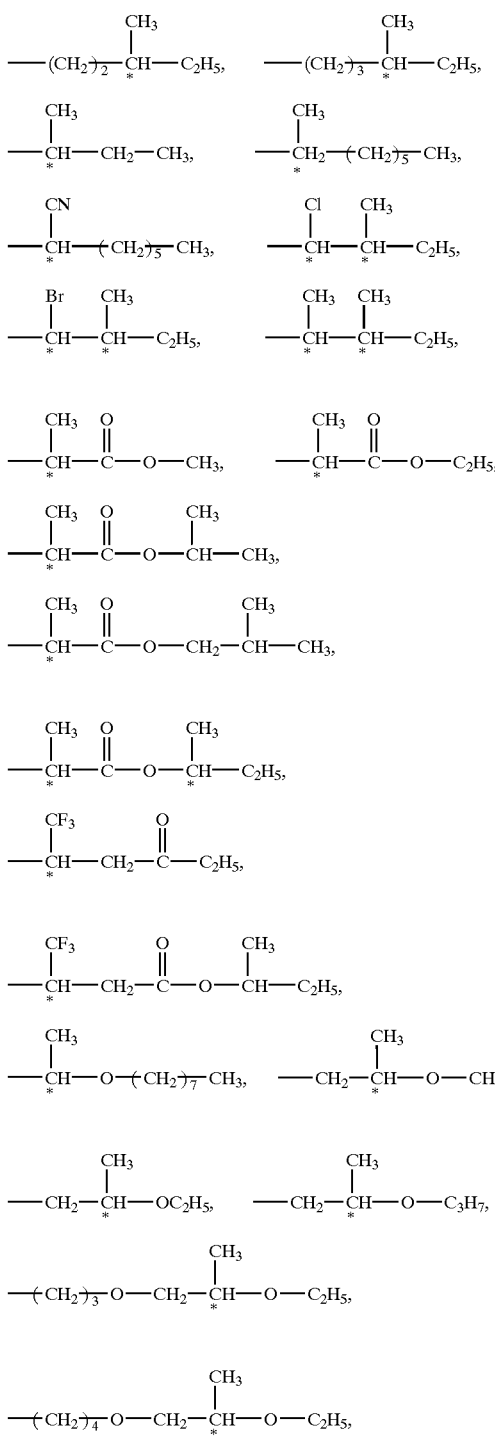

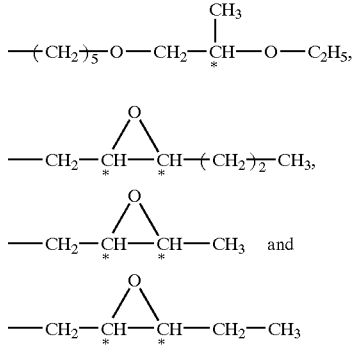

With very particular preference, component III of the copolyisocyanates that can be employed is derived from 2,6-dimethylheptyl isocyanate.

The radical $R^2$ of the copolyisocyanates that can be employed is preferably selected from $C_3$–$C_{11}$-alkenyl radicals, $C_4$–$C_{11}$-vinyl ether radicals (=vinyl $C_2$–$C_9$-alkyl ethers), ethylenically unsaturated $C_3$–$C_{11}$ carboxylic acid radicals and esters of ethylenically unsaturated $C_3$–$C_6$ monocarboxylic acids with $C_2$–$C_6$-alkanols, the linkage to the nitrogen taking place via the alkanol residue of the ester. The radical is with particular preference selected from methyl acrylate, ethyl acrylate, propyl acrylate, n-butyl acrylate, isobutyl acrylate, 2-ethylhexyl acrylate, methyl methacrylate, ethyl methacrylate, propyl methacrylate, n-butyl methacrylate, isobutyl methacrylate, and 2-ethylhexyl methacrylate, especially from ethyl acrylate or ethyl methacrylate.

The radical $R^3$ preferably has the same definitions as the radical $R^1$. However, it is achiral, i.e. it has no center of chirality or is in the form of a racemic mixture.

With particular preference, the main chain of the radical $R^3$ has a length of from 4 to 12, in particular 6 to 10, preferably 6 to 8 members (carbons, oxygens and/or sulfurs). Component V of the copolyisocyanates of the invention is, with very particular preference, derived from n-hexyl isocyanate, n-heptyl isocyanate or n-octyl isocyanate.

Components III, IV and V are preferably present in a molar ratio III:IV:V of about 1 to 20:1 to 20:50 to 98, in particular about 5 to 15:5 to 15:65 to 90, and, with particular preference, about 15:10:75.

The units III, IV and V can be distributed randomly in the copolyisocyanates which can be employed.

Very particular preference is given, in accordance with the invention, to the presence in $A^1$ and $A^2$ of chiral compounds and nematic monomers of group b), especially of chiral compounds of the formula 2:

(2)

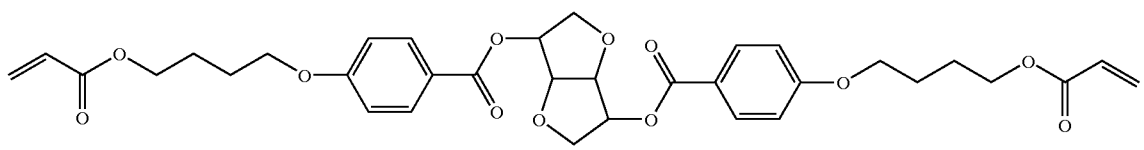

or of the formula 5:

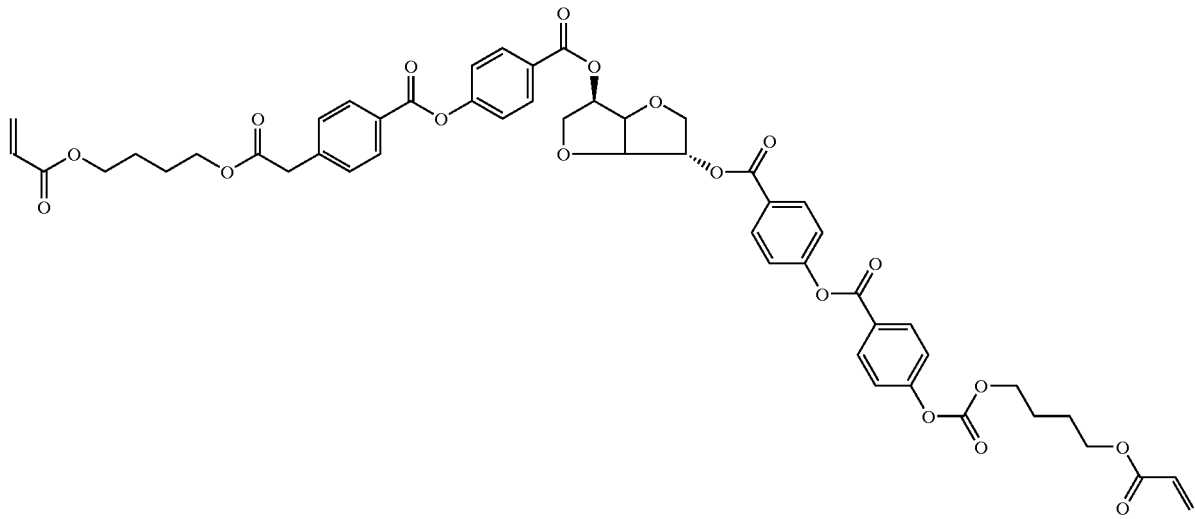

and nematic monomers of the formula 1:

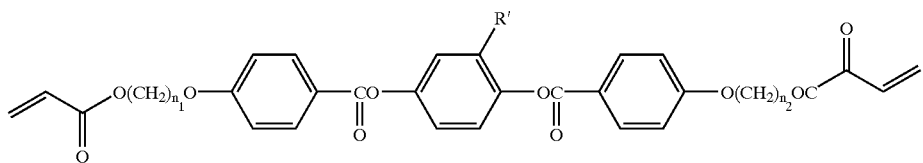

or preferably of the formula 3:

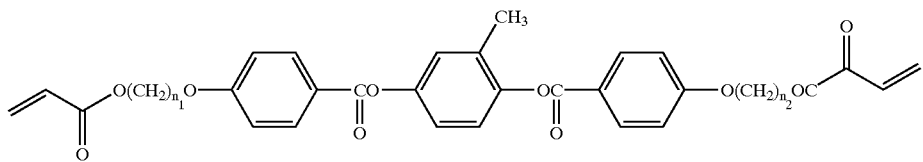

or with particular preference of the formula 4:

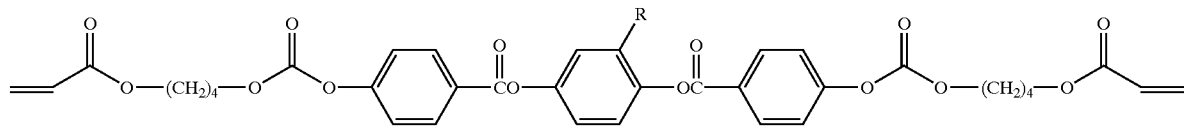

in the cured state, where $n_1$ and $n_2$ in formulae 1 and 3 are independently 4 or 6, R' in formula 1 is H or Cl and the monomers of the formula 1 or 3 are preferably employed as mixtures of the compounds with $n_1/n_2$=4/4, 4/6, 6/4 or 6/6, and R in formula 4 is H, Cl or $CH_3$. It is also possible in accordance with the invention, however, for other cholesteric mixtures, examples being the mixtures disclosed in EP-A-686 674, to be present in the cured state in $A^1$ and $A^2$.

The cholesteric mixtures, and the formulations comprising the absorption pigment, can be diluted with any suitable diluent before being applied to the carrier.

Diluents which can be employed in the process of the invention for the compounds of the groups a) and b) are linear or branched esters, especially acetic esters, cyclic ethers and esters, alcohols, lactones, aliphatic and aromatic hydrocarbons, such as toluene, xylene and cyclohexane, and also ketones, amides, N-alkylpyrrolidones, especially N-methylpyrrolidone, and in particular tetrahydrofuran (THF), dioxane and methyl ethyl ketone (MEK).

Examples of suitable diluents for the polymers of group c) are ethers and cyclic ethers, such as tetrahydrofuran or dioxane, chlorinated hydrocarbons, such as dichloromethane, 1,1,2,2-tetrachloroethane, 1-chloronaphthalene, chlorobenzene or 1,2-dichlorobenzene. These diluents are particularly suitable for polyesters and polycarbonates. Examples of suitable diluents for cellulose derivatives are ethers, such as dioxane, or ketones, such as acetone. If copolyisocyanates are employed as polymers of group d) it is advisable to use polymerizable diluents as described in U.S. Pat. No. 8,834,745. Examples of such polymerizable diluents are

- esters of α,β-unsaturated mono- or dicarboxylic acids, especially $C_3$–$C_6$ mono- or dicarboxylic acids, with $C_1$–$C_{12}$-alkanols, $C_2$–$C_{12}$-alkanediols or their $C_1$–$C_6$-alkyl ethers and phenyl ethers, for example the acrylates and methacrylates, hydroxyethyl or hydroxypropyl acrylate or methacrylate, and 2-ethoxyethyl acrylate or methacrylate;
- vinyl $C_1$–$C_{12}$-alkyl ethers, such as vinyl ethyl$^1$, vinyl hexyl or vinyl octyl ether;
- vinyl esters of $C_1$–$C_{12}$ carboxylic acids, such as vinyl acetate, vinyl propionate, vinyl laurate;
- $C_3$–$C_9$ epoxides, such as 1,2-butylene oxide, styrene oxide;
- N-vinylpyrrolidone, N-vinylcaprolactam, N-vinylformamide;
- vinylaromatic compounds, such as styrene, α-methylstyrene, chlorostyrene, and
- compounds having two or more crosslinkable groups, such as diesters of diols (including polyethylene glycols) with acrylic or methacrylic acid, or divinylbenzene.

Examples of preferred polymerizable diluents are 2-ethoxyethyl acrylate, diethylene glycol diacrylate, ethylene glycol dimethacrylate, diethylene glycol dimethacrylate, triethylene glycol dimethacrylate, diethylene glycol monomethyl ether acrylate, phenoxyethyl acrylate and tetraethylene glycol dimethacrylate. A particularly preferred polymerizable diluent is styrene.

The mixtures of groups a), b) or c) may also include, in small amounts, polymerizable diluents in addition to the inert diluent. Preferred polymerizable solvents which can be added to a), b) or c) are acrylates, especially acrylates of relatively high functionality such as bis-, tris- or tetraacrylates, and with particular preference high-boiling oligoacrylates. The preferred amount added is approximately 5% by weight, based on the overall weight of the mixture.

Water may also be added to the diluent or even employed as the diluent alone.

For photochemical polymerization, the cholesteric mixture may include customary commercial photoinitiators. For curing by electron beams, such initiators are not required. Examples of suitable photoinitiators are isobutyl benzoin ether, 2,4,6-trimethylbenzoyldiphenylphosphine oxide, 1-hydroxycyclohexyl phenyl ketone, 2-benzyl-2-dimethylamino-1-(4-morpholinophenyl)furan-1-one, mixtures of benzophenone and 1-hydroxycyclohexyl phenyl ketone, 2,2-dimethoxy-2-phenylacetophenone, perfluorinated diphenyltitanocenes, 2-methyl-1-(4-[methylthio]-phenyl)-2-(4-morpholinyl)-1-propanone, 2-hydroxy-2-methyl-1-phenylpropan-1-one, 4-(2-hydroxyethoxy)phenyl 2-hydroxy-2-propyl ketone, 2,2-diethoxyacetophenone, 4-benzoyl-4'-methyl-diphenyl sulfide, ethyl 4-(dimethylamino)benzoate, mixtures of 2-isopropylthioxanthone and 4-isopropylthioxanthone, 2-(dimethylamino)ethyl benzoate, d,l-camphorquinone, ethyl-d,l-camphorquinone, mixtures of benzophenone and 4-methylbenzophenone, benzophenone, 4,4'-bisdimethylaminobenzophenone, ($\eta^5$-cyclopentadienyl)($\eta^6$-isopropylphenyl)iron(II) hexafluorophosphate, triphenylsulfonium hexafluorophosphate or mixtures of triphenylsulfonium salts, and also butanediol diacrylate, dipropylene glycol diacrylate, hexanediol diacrylate, 4-(1,1-dimethylethyl)cyclohexyl acrylate, trimethylolpropane triacrylate and tripropylene glycol diacrylate.

The brightness of the cholesteric layers $A^1$ and $A^2$ can be increased by adding small amounts of suitable leveling agents. It is possible to employ from about 0.005 to 1% by weight, in particular from 0.01 to 0.5% by weight, based on the amount of cholesteric employed. Examples of suitable leveling agents are glycols, silicone oils and, in particular, acrylate polymers, such as the acrylate copolymers obtainable under the name Byk 361 or Byk 358 from Byk-Chemie and the modified, silicone-free acrylate polymers obtainable under the name Tego flow ZFS 460 from Tego.

The cholesteric mixture may also include stabilizers to counter the effects of UV and weather. Examples of suitable such additives are derivatives of 2,4-dihydroxybenzophenone, derivatives of 2-cyano-3,3-diphenyl acrylate, derivatives of 2,2',4,4'-tetrahydroxybenzophenone, derivatives of ortho-hydroxyphenylbenzotriazole, salicylic esters, ortho-hydroxyphenyl-S-triazines or sterically hindered amines. These substances can be employed alone or, preferably, as mixtures.

The present invention additionally provides a process for producing a pigment of the invention, which comprises applying the layers $A^1$, B and $A^2$ atop one another to a substrate, simultaneously or with a time differential, curing the layers by heat, UV radiation, electron beams or by rapid cooling to below the glass transition temperature, simultaneously or with a time differential, removing the fully cured layers from the substrate, and then comminuting them to give pigments.

The application of the layers $A^1$, B and $A^2$ to the substrate can be carried out by means of customary techniques selected, for example, from air-knife coating, knife coating, air blade coating, squeeze coating, impregnation, reverse roll coating, transfer roll coating, gravure coating, kiss coating, casting, spray coating, spin coating or printing techniques, such as letterpress (relief), intaglio, flexographic, offset or screen printing. The layers $A^1$, B and $A^2$ are preferably applied to the substrate by means of casting or offset printing.

The substrate is preferably mobile and with particular preference is a moving substrate in strip form.

Suitable layer substrates are, preferably, known films formed from polyesters, such as polyethylene terephthalate or polyethylene naphthalate, and also polyolefins, cellulose triacetate, polycarbonates, polyamides, polyimides, polyamidoimides, polysulfones, aramids or aromatic polyamides. The thickness of the layer substrates is preferably from about 5 to 100 μm, in particular from about 10 to 20 μm. The layer substrate can be subjected beforehand to a corona discharge treatment, a plasma treatment, a gentle adhesion treatment, a heat treatment, a dedusting treatment or the like. The layer substrate preferably has a mean center-line surface roughness of 0.03 μm or less, in particular of 0.02 μm or less, and, with particular preference, 0.01 μm or less. It is is desirable, moreover, for the substrate to have not only a low mean center-line surface roughness of this kind but also to possess no great projections (raised areas) of 1 μm or more. The roughness profile of the surface of the substrate can be varied by means of fillers which are added to the layer substrate in the course of its production. Examples of suitable fillers are oxides and carbonates of Ca, Si and Ti, and fine organic powders of acrylic substances.

The substrate can also be a metallized foil or a preferably polished metal strip.

The layers $A^1$, B and $A^2$ can be of low or high viscosity, but are preferably of low viscosity, when they are applied to the substrate. For this purpose, the cholesteric mixtures, or the formulations comprising absorption pigment, can be applied to the carrier in indiluted or minimally diluted form at elevated temperature or in highly diluted form at a low temperature. It is particularly preferred to apply the three layers $A^1$, B and $A^2$ wet-on-wet to the carrier in one operation, then to dry them together, if appropriate, and subsequently to subject them to conjoint curing.

For the simultaneous application wet-on-wet of said layers it is particularly preferred if the layer B comprises absorption pigments bound in a matrix of the same cholesteric mixture as is also present in the layers $A^1$ and $A^2$. By this means, possibly disruptive layer boundaries between $A^1$, B and $A^2$ are avoided, so giving a homogeneous system which comprises homogenously distributed pigments in the central region.

Casting techniques are particularly suitable for the simultaneous application of said layers, especially knife or bar coating processes, cast-film extrusion or stripping processes, and the cascade coating process.

In the case of the knife or bar coating process, the liquid is applied to a substrate through a slot in a casting block, the layer thickness being adjustable by way of a defined knife or bar gap between a roller, over which the carrier is guided, and the lip of the coater. To apply the bottom (first) layer, the first casting block is brought toward the roller; to apply the second layer, a second casting block is brought toward the first casting block and, to apply the third layer, a third casting block is brought against the second. An analogous process is described in DE-A-19 504 930, which is incorporated herein by reference. All three liquids run to their respective coating blade or bar and are coated out simultaneously over one another.

In the case of the cast-film extrusion or stripping process, a flexible substrate, such as a film, is guided past the coater head under defined web tension between two rollers. The amounts of liquid appropriate to the desired layer thickness are applied simultaneously to the substrate from three parallel casting slots arranged transverse to the running direction of the web. A process of this kind is described, for example, in EP-A 431 630, DE-A-3 733 031 and EP-A-452 959, which are incorporated herein by reference.

In the cascade coating process, the substrate is guided over a roller. The liquids to be applied run over one another from differently arranged slots and then run together on the carrier. This process is likewise described in DE-A-19 504 930.

It is of course also possible first to apply only one cholesteric layer, to subject this layer, if desired, to drying and to curing, and then to apply two layers wet-on-wet to the cured cholesteric layer by means, for example, of one of the abovementioned processes. It is likewise possible to subject each layer to individual and successive application, optional drying and curing.

If casting techniques are employed, the pourable cholesteric mixture preferably has a viscosity in the range from about 10 to 500 mPas, in particular from about 10 to 100 mpas, measured at 23° C. The cholesteric mixture is, with particular preference, applied to the substrate at a rate from about 1 to 800 m/min, in particular from about 5 to 100 m/min. It is preferred to use a casting apparatus whose casting slot width is in the range from about 2 to 50 μm, in particular from about 4 to 15 μm. The cholesteric mixture is preferably applied under elevated pressure, in particular at a coater overpressure in the range from about 0.01 to 0.7 bar, with particular preference from 0.05 to 0.3 bar.

The cured layers can be removed from the substrate, for example, by guiding the substrate over a deflecting roller having a small diameter. As a consequence of this the crosslinked material then peels away from the substrate. Other known methods are equally suitable: for example, the stripping of the substrate over a sharp edge, or by way of an air knife, ultrasound or combinations thereof. The cholesteric material, now devoid of its substrate, is comminuted to a desired particle size. This can be done, for example, by grinding in universal mills. In order to narrow the particle size distribution the comminuted pigments can subsequently be classified by means, for example, of a sieving process.

The invention additionally provides compositions comprising pigments of the invention.

Particularly preferred compositions of the invention are coating materials, such as paints and varnishes, which comprise not only the pigments of the invention but also one or more substances selected from waterborne coatings, for example in the form of aqueous dispersions, such as PMA, SA, polyvinyl derivatives, PVC, polyvinylidene chloride, SB copolymer, PV-AC copolymer resins, or in the form of water-soluble binders, such as shellac, maleic resins, rosin-modified phenolic resins, linear and branched, saturated polyesters, amino resin-crosslinking saturated polyesters, fatty acid-modified alkyd resins, plasticized urea resins, or in the form of water-thinnable binders, such as PU dispersions, EP resins, urea resins, melamine resins, phenolic resins, alkyd resins, alkyd resin emulsions, silicone resin emulsions; powder coatings, such as powder coatings for TRIBO/ES, such as polyester coating powder resins, PU coating powder resins, EP coating powder resins, EP/SP hybrid coating powder resins, PMA coating powder resins, or powder coatings for fluidized-bed sintering, such as thermoplasticized EPS, LD-PE, LLD-PE, HD-PE; solventborne coatings, such as one- and two-component coating materials (binders) examples being shellac, rosin esters, maleate resins, nitrocelluloses, rosin-modified phenolic resins, physically drying saturated polyesters, amino resin-crosslinking saturated polyesters, isocyanate-crosslinking saturated polyesters, self-crosslinking saturated polyesters, alkyds with saturated fatty acids, linseed oil alkyd resins, soya oil resins, sunflower oil alkyd resins, safflower oil alkyd resins, ricinene alkyd resins, tung oil/linseed oil alkyd resins, mixed-oil alkyd resins, resin-modified alkyd resins, styrene/vinyltoluene-modified alkyd resins, acrylicized alkyd resins, urethane-modified alkyd resins, silicone-modified alkyd resins, epoxy-modified alkyd resins, isophthalic acid alkyd resins, unplasticized urea resins, plasticized urea resins, melamine resins, polyvinyl acetals, non-crosslinking P(M)A homo- or copolymers, noncrosslinking P(M)A homo- or copolymers with nonacrylic monomers, self-crosslinking P(M)A homo- or copolymers, P(M)A copolymers with other nonacrylic monomers, externally crosslinking P(M)A homo- or copolymers, externally crosslinking P(M)A copolymers with nonacrylic monomers, acrylate copolymer resins, unsaturated hydrocarbon resins, organic-soluble cellulose compounds, silicone combination resins, PU resins, P resins, peroxide-curing unsaturated synthetic resins, radiation-curing synthetic resins, both photoinitiator-containing and photoinitiator-free radiation-curing synthetic resins; solvent-free coating materials (binders) such as isocyanate-crosslinking saturated polyesters, two-pack PU resin systems, moisture-curing 1-component PU resin systems, EP resins, and also synthetic resins—individually or in combination—such as acrylonitrile-butadiene-styrene-copolymers, BS, cellulose acetate, cellulose acetobutyrate, cellulose acetopropionate cellulose nitrate, cellulose propionate, artificial horn, epoxy resins, polyamide, polycarbonate, polyethylene, polybutylene terephthalate, polyethylene terephthalate, polymethyl methacrylate, polypropylene, polystyrene, polytetrafluoroethylene, polyvinyl chloride, polyvinylidene chloride, polyurethane, styrene-acrylonitrile copolymers, or unsaturated polyester resins in the form of granules, powders or casting resin.

The compositions of the invention may additionally comprise stabilizers to counter the effects of UV and weather, and also inorganic or organic pigments, as described above.

The pigments of the invention can be incorporated individually or in mixtures into the compositions of the invention where they may if desired be subjected to additional alignment by methods which initiate shear forces. Suitable methods of aligning the pigments of the invention are printing and knife coating or, in the case of magnetic pigments, applying an external magnetic field.

The present invention additionally provides coating materials comprising at least one multilayer pigment of the invention, preferably coating materials selected from effect paints, effect inks or effect films, and especially from self-opacifying effect paints, inks or films.

The present invention also provides for the use of the pigments of the invention in the vehicle and vehicle accessories sector, in the EDT, in the leisure, sport and games sector, as an optical component such as a polarizer or filter in the cosmetics field, in the textile, leather or jewelry field, in the gift product field, in writing utensils, packaging or spectacle frames, in the construction sector, in the household sector and in connection with printed products of all kinds, such as cardboard packaging, other packaging materials, carrier bags, papers, labels or sheets, or for preparing inks and paints.

The color effects which can be achieved by means of the cholesteric pigments of the invention embrace—owing to the host of achievable reflection wavelengths—the UV and IR region as well as, of course, the region of visible light. If the pigments of the invention are applied to or incorporated into bank notes, cheque cards, other cashless means of payment or ID (by means, for example, of known printing techniques), this considerably hinders the identical copying, and especially the counterfeiting, of these articles. The present invention therefore additionally provides for the use of the pigments of the invention for the anticounterfeiting treatment of articles, especially bank notes, cheque cards or other cashless means of payment or ID.

Also provided for by the present invention is the use of the compositions of the invention for coating articles of utility and for painting vehicles.

The invention will now be illustrated on the basis of the following working examples and with reference to attached FIG. 1. Here, FIG. 1 shows the diagrammatic representation of a coating apparatus which can be employed in accordance with the invention.

EXAMPLE 1

Preparing Three-layer Pigments with a Pigmented Absorber Layer Comprising a Cholesteric Radiation-curable Binder a) Preparing the 1st Cholesteric Layer A cholesteric mixture of the above-described group b) was employed, which comprised a compound of the above formula 2 as chiral monomer and a mixture of compounds of the above formula 3 as achiral, nematic monomer. The undiluted cholesteric mixture contained 90.5% by weight of the achiral, nematic compound, 6.5% by weight of the chiral compound and, as photoinitiator, 3% by weight of 1-hydroxycyclohexyl phenyl ketone, which is marketed under the name Irgacure 184. The solvent used was methyl ethyl ketone.

Coating was carried out with a coating apparatus which is represented diagrammatically in FIG. 1. A glossy black polyethylene terephthalate film (PET film) (G) already coated on its reverse face and having a thickness of 15 μm was unrolled continuously from the film winder (F) and was coated with a blade coater. The thickness of the cholesteric layer was 2 μm. Drying took place at 60° C. in the dryer (C). The layer was cured by UV fixing in the UV unit (A), while the dried strip was guided over the cooling roll (B). The cured cholesteric layer was wound up onto the roller (D).

The reflection maximum of the layer was at 520 nm.

b) Preparing an Absorber Layer Pigmented with Carbon Black, with a Cholesteric Binder 150 g of pigment-grade carbon black Regal 400R (manufacturer: Cabot Corporation) are kneaded for 1 hour with 3 g of stearic acid, 80 g of a phosphonate-functional dispersing resin (50% strength in tetrahydrofuran, described in DE-A-195 16 784) and 40 g of methyl ethyl ketone in a laboratory compounder having a capacity of 300 ml. The resulting kneaded mass (solids content 70.7%) is subsequently adjusted to a solids content of 25% in a dissolver, using 499 g of methyl ethyl ketone. This dispersion is then fully dispersed to the optimum extent in a stirred mill (model Dispermat SL, milling chamber volume 125 ml, grinding media zirconium oxide 1–1.25 mm). The progress of dispersion during this step is monitored by means of an interference contrast technique (EP-B-0-032-710). The ultimate fineness is achieved when the surface to be tested is agglomerate-free. A layer prepared from this dispersion is highly glossy and has a base roughness of ≦100 nm. 500 g of a 60% strength cholesteric solution together with 0.3 g of Byk 361 (Byk-Chemie) are mixed thoroughly into the resultant dispersion for 30 minutes using a dissolver. Following the stirred incorporation of 9 g of photoinitiator Irgacure 907 (Ciba Geigy) this dispersion (solids content 39.2%) can be applied. For this purpose, it is applied in a layer thickness of 0.8 μm (dry thickness) to the 1st cholesteric layer in analogy to step a), is physically dried, and then is radiation-cured under a nitrogen atmosphere.

c) Preparing the 2nd Cholesteric Layer

A further cholesteric layer is applied in analogy to step a) to the cured absorber layer, and is dried and cured. In terms of its composition and layer thickness, the 2nd cholesteric layer is comparable with the 1st cholesteric layer.

d) Preparing Pigments

The cured three-layer assembly is removed from the carrier film by being damaged with a razor blade transverse to the film web direction and then blown off with compressed air, which is injected through a slot die. In the course of this procedure, the coated film is guided continuously past the slot die and the three-layer assembly removed by blowing is collected in the form of flakes. The three-layer flakes are 6 μm thick and on both sides, when viewed straight on, show a strong green color with a color change to blue when the flakes are viewed at an oblique angle.

10 g of cholesteric flakes are mixed with 100 g of sodium chloride and the mixture is milled 6 times for 2 minutes in a beater blade mill. After milling, the salt is washed out with water and the pigment is isolated.

The pigment prepared in this way possesses a high brightness on both sides with a coloredness which is dependent on the viewing angle.

EXAMPLE 2

Preparing Cholesteric Three-layer Pigments without a Cholesteric Interlayer a) Preparing the 1st Cholesteric Layer With the aid of a coater apparatus as in Example 1, a solution consisting of 45 parts of cholesteric mixture (96.2% nematic component of formula (3) and 3.8% chiral component of formula (5)), 3 parts of photoinitiator Irgacure® 907 (from Ciba-Geigy), 0.1 part of Byk 361 (from Byk) and 51.9 parts of methyl ethyl ketone are applied to a polyester film. The coated film is then passed through a drying tunnel which is thermostated at 60° C. Subsequently, the physically dried layer is cured in-line by radiation with UV light under a nitrogen atmosphere, and the coated film is wound up onto a spool. The cholesteric layer has a thickness of 2 μm and, vertically to the plane of the layer, reflects light, with a reflection maximum at a wavelength of 505 nm. When viewed with the eye, the layer appears green when viewed straight on with a color change to blue when the layer is viewed at an oblique angle.

b) Preparing the Interlayer

The film coated as described under a) is coated, using the same coater apparatus, with a solution consisting of 70.82 parts of black printing ink Flexoplastol VA/2-black (from BASF AG), 7.08 parts of reactive diluent (triacrylate of propoxylated/ethoxylated trimethylolpropane; Laromer® PO 33F from BASF AG), 0.85 part of photoinitiator Irgacure® 500 (from Ciba-Geigy), and 21.25 parts of tetrahydrofuran. The coated film is then passed through a drying tunnel which is thermostated to 60° C., and the film is physically dried. Subsequently, the layer is cured in-line by radiation with UV light under a nitrogen atmosphere and the coated film is wound up onto a spool. The black layer has a thickness of 1 μm.

c) Preparing the 2nd Cholesteric Layer

The film coated as described under a) and b) is coated, using the same coater apparatus, with a solution consisting of 45 parts of cholesteric mixture (cf. step a)), 3 parts of photoinitiator Irgacure® 907, 0.1 part of Byk 361 and 51.9 parts of methyl ethyl ketone. The coated film is then passed through a drying tunnel which is thermostated at 60° C., and the film is physically dried. Subsequently, the layer is cured in-line by radiation with UV light under a nitrogen atmosphere and the coated film is wound up onto a spool. The cholesteric layer has a thickness of 2 μm and, vertically to the plane of the layer, reflects light, with a reflection maximum at 510 nm. When viewed with the eye, the layer appears green when viewed straight on with a color change to blue when the layer is viewed at an oblique angle.

In accordance with the operating steps a), b) and c), a 3-layer assembly is obtained on the polyester carrier film. The mechanical stability of the 3-layer assembly was determined by measuring the tear strength and the peel force. For this purpose, the films coated with the 3-layer assembly were cut into 3.81 mm wide strips, the force transducer was stuck to the three-layer assembly, and the force required to tear (tear strength) or to peel (peel strength) the already torn layer is measured. The tear strength between the first cholesteric layer and the black interlayer is 0.065 N and the peel strength is 0.005 N.

d) Removing the Three-layer Assembly From the Carrier Film

The three-layer assembly described under a), b) and c) is removed from the polyester carrier film by damaging the three-layer structure with a razor blade transversely to the film web direction and then blowing it off with compressed air, which is injected through a slot die. In the course of this operation, the coated film is guided continuously past the slot die and the three-layer assembly removed by blowing is collected in the form of flakes. The three-layer flakes are 6 μm thick and on both sides, when viewed straight on, show a strong green color with a color change to blue when the flakes are viewed at an oblique angle.

e) Milling the Three-layer Flakes to a Pigment 10 g of cholesteric flakes prepared as described under d) are mixed with 100 g of sodium chloride and the mixture is milled 6 times for 2 minutes in a beater blade mill. After milling, the salt is washed off with water and the pigment is isolated. In the course of milling, there is partial delamination of the three-layer pigment.

EXAMPLE 3

Preparing Cholesteric Three-layer Pigments without a Cholesteric Interlayer a) First of All, the 1st Cholesteric Layer is Prepared as Described in Example 2 Under a).

b) Preparing the Interlayer

The film coated as described under a) is coated, using the same coater apparatus, with a solution consisting of 28.33 parts of black printing ink Flexoplastol VA/2-black (from BASF AG), 2.83 parts of reactive diluent (Laromer® PO 33F from BASF AG), 0.34 part of photoinitiator Irgacure® 500 (from Ciba-Geigy), 60 parts of a 20 percent strength solution of a copolymer of ethylhexyl acrylate and acrylic acid; Acronal® 101 L from BASF AG) in tetrahydrofuran, and 8.5 parts of tetrahydrofuran. The coated film is then passed through a drying tunnel which is thermostated to 60° C., and the film is physically dried. Subsequently, the layer is cured in-line by radiation with UV light under a nitrogen atmosphere and the coated film is wound up onto a spool. The black layer has a thickness of 1 μm.

c) Preparing the 2nd Cholesteric Layer

The 2nd cholesteric layer is applied to the black interlayer as described in Example 2 under c), to give a three-layer assembly. The test of the mechanical stability of the three-layer assembly gives a tear strength between the 1st cholesteric layer and the black interlayer of 0.19 N and a peel force of 0.01 N.

d) Removing the Three-layer Assembly From the Carrier Film

The three-layer assembly is removed from the carrier film as described in Example 2 under d).

e) Milling the Three-layer Flakes to a Pigment

Milling to a pigment takes place as described in Example 2 under e). Microscopic evaluation indicates a much smaller proportion than in Example 2 of delaminated pigment particles which are 6 μm thick and show a strong green color on both sides when viewed straight on. If the viewing angle is changed, then a color change from green to blue is obtained.

When viewed against a white background, the pigment particles are opaque.

We claim:

1. A platelet-shaped cholesteric multilayer pigment which comprises the layer sequence $A^1/B/A^2$, wherein $A^1$ and $A^2$ are identical or different and each comprise at least one cholesteric layer wherein the thickness of each cholesteric layer is about 0.5 to 2 μm, and B is at least one interlayer which separates the layers $A^1$ and $A^2$ from one another and which absorbs all or some of the light transmitted by the layers $A^1$ and $A^2$.

2. A multilayer pigment as claimed in claim 1, wherein $A^1$ and $A^2$ possess identical or different optical properties.

3. A multilayer pigment as claimed in claim 2, wherein $A^1$ and $A^2$ reflect light of identical or different wavelength and/or are of identical or different handedness.

4. A multilayer pigment as claimed in claim 1, wherein B comprises at least one organic or inorganic absorption pigment, optionally bound in a binder matrix.

5. A multilayer pigment as claimed in claim 1, wherein $A^1$ and $A^2$ comprise cholesteric mixtures selected from the group consisting of a) at least one cholesteric, polymerizable monomer, b) at least one achiral, nematic, polymerizable monomer and one chiral compound, c) at least one cholesteric, crosslinkable oligomer or polymer, d) a cholesteric polymer in a polymerizable diluent, and e) at least one cholesteric polymer whose cholesteric phase can be frozen in by rapid cooling to below the glass transition temperature, in the cured state.

6. A multilayer pigment as claimed in claim 1, wherein B comprises a binder matrix comprising at least one cholesteric mixture selected from the group consisting of a) at least one cholesteric, polymerizable monomer, b) at least one achiral, nematic, polymerizable monomer and one chiral compound, c) at least one cholesteric, crosslinkable oligomer or polymer, d) a cholesteric polymer in a polymerizable diluent, and e) at least one cholesteric polymer whose cholesteric phase can be frozen in by rapid cooling to below the glass transition temperature, in the cured state.

7. A multilayer pigment as claimed in claim 6, where $A^1$, B and A2 comprise the same cholesteric mixtures.

8. A process for producing a multilayer pigment as claimed in claim 1, which comprises applying the layers $A^1$, B and $A^2$ atop one another to a substrate, simultaneously or with a time differential, curing the layers, simultaneously or with a time differential, removing the fully cured layers from the substrate and then comminuting them to produce multilayer pigments.

9. A process as claimed in claim 8, wherein the applied layers are dried prior to curing.

10. A process as claimed in claim 8, which comprises applying the layers $A^1$, B and $A^2$ to the substrate by means of a technique selected from the group consisting of air knife.

11. A process as claimed in claim 10, which comprises applying the layers $A^1$, B and $A^2$ to the substrate by means of letterpress (relief), intaglio, flexographic, or offset or screen printing.

12. A process as claimed in claim 10, wherein the layers $A^1$, B and $A^2$ are applied by means of casting or offset printing.

13. A composition comprising at least one multilayer pigment as claimed in claim 1.

14. A coating material comprising at least one multilayer pigment as claimed in claim 1.

* * * * *